(12) United States Patent
Andolina et al.

(10) Patent No.: US 11,802,313 B2
(45) Date of Patent: *Oct. 31, 2023

(54) MITOCHONDRIAL HEALTH PARAMETERS AS CLINICAL PREDICTORS OF PARKINSON'S DISEASE

(71) Applicant: University of Pittsburgh—Of the Commonwealth System of Higher Education, Pittsburgh, PA (US)

(72) Inventors: Laurie H. Andolina, Durham, NC (US); John T. Greenamyre, Sewickley, PA (US); Sruti Shiva, Sewickley, PA (US)

(73) Assignee: University of Pittsburgh—Of the Commonwealth System of Higher Education, Pittsburgh, PA (US)

( * ) Notice: Subject to any disclaimer, the term of this patent is extended or adjusted under 35 U.S.C. 154(b) by 280 days.

This patent is subject to a terminal disclaimer.

(21) Appl. No.: 17/227,186

(22) Filed: Apr. 9, 2021

(65) Prior Publication Data

US 2021/0254162 A1  Aug. 19, 2021

Related U.S. Application Data

(63) Continuation of application No. 15/758,695, filed as application No. PCT/US2016/050773 on Sep. 8, 2016, now Pat. No. 11,001,890.

(60) Provisional application No. 62/271,911, filed on Dec. 28, 2015, provisional application No. 62/216,199, filed on Sep. 9, 2015.

(51) Int. Cl.
*C12Q 1/68* (2018.01)
*C12Q 1/6883* (2018.01)
*C12Q 1/686* (2018.01)

(52) U.S. Cl.
CPC ........... *C12Q 1/6883* (2013.01); *C12Q 1/686* (2013.01); *C12Q 2561/113* (2013.01); *C12Q 2563/173* (2013.01); *C12Q 2600/106* (2013.01)

(58) Field of Classification Search
CPC ................. C12Q 1/6883; C12Q 1/686; C12Q 2561/113; C12Q 2563/173
See application file for complete search history.

(56) References Cited

U.S. PATENT DOCUMENTS

| 8,058,431 | B2 | 11/2011 | Josel et al. |
| 11,001,890 | B2* | 5/2021 | Andolina ............... C12Q 1/686 |
| 2009/0075269 | A1 | 3/2009 | Caplin |
| 2009/0275037 | A1 | 11/2009 | Josel et al. |

FOREIGN PATENT DOCUMENTS

| WO | WO 2013/023144 A2 | 2/2013 |
| WO | WO 2014/090762 A1 | 6/2014 |

OTHER PUBLICATIONS

Ayala-Torres et al., "Analysis of gene-specific DNA damage and repair using guantitative polymerase chain reaction," *Methods* 22(2): 135-147 (Oct. 2000).
Furda et al., "Quantitative PCR-based measurement of nuclear and mitochondrial DNA damage and repair in mammalian cells," *Methods in Molecular Biology* 1105:419-437 (2014).
International Search Report from PCT Application No. PCT/US2016/050773, 5 pages (dated Nov. 7, 2016).
Kovalenko and Santos, "Analysis of oxidative damage by gene-specific quantitative PCR," *Current Protocols in Human Genetics* Supplement 62: 13 pages (published online Jul. 2009).
Lehle et al., "Lord-Q: a long-run real-time PCR-based DNA-damage quantification method for nuclear and mitochondrial genome analysis," *Nucleic Acids Research* 42(6): e41, 12 pages (published online Dec. 26, 2013).
Sanders et al., "LRRK2 mutations cause mitochondrial DNA damage in iPSC-derived neural cells from Parkinson's disease patients: Reversal by gene correction", *Neurobiology of Disease* 62: 381-386 (published online Oct. 19, 2013).
Sanders et al., "Mitochondrial DNA damage: molecular marker of vulnerable nigral neurons in Parkinson's disease," *Neurobiology of Disease* 70: 214-223 (published online Jun. 27, 2014).
Written Opinion from PCT Application No. PCT/US2016/050773, 5 pages (dated Nov. 7, 2016).

* cited by examiner

*Primary Examiner* — Jezia Riley
(74) *Attorney, Agent, or Firm* — KLARQUIST SPARKMAN, LLP

(57) ABSTRACT

Methods are disclosed for detecting peripheral mitochondrial DNA damage and dysfunction. Methods are also disclosed that utilize blood samples to detect a neurodegenerative disease, such as Parkinson's disease, and determine the efficacy of therapy.

27 Claims, 5 Drawing Sheets

Specification includes a Sequence Listing.

FIG. 1
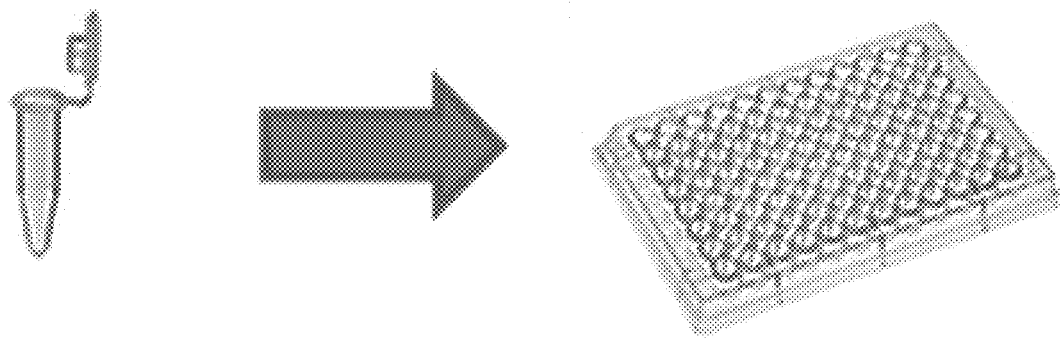
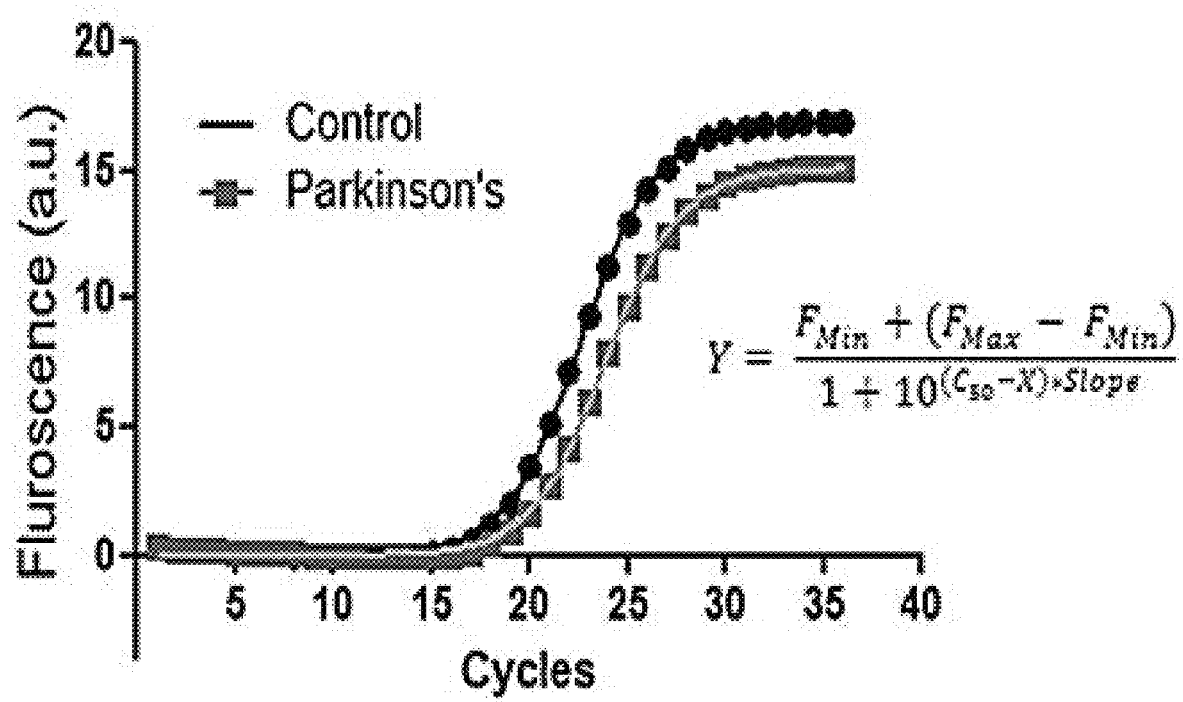
$$Y = \frac{F_{Min} + (F_{Max} - F_{Min})}{1 + 10^{(C_{50}-X) \times Slope}}$$

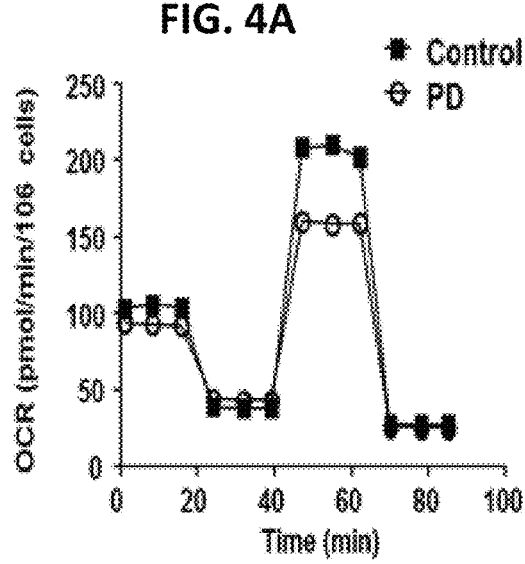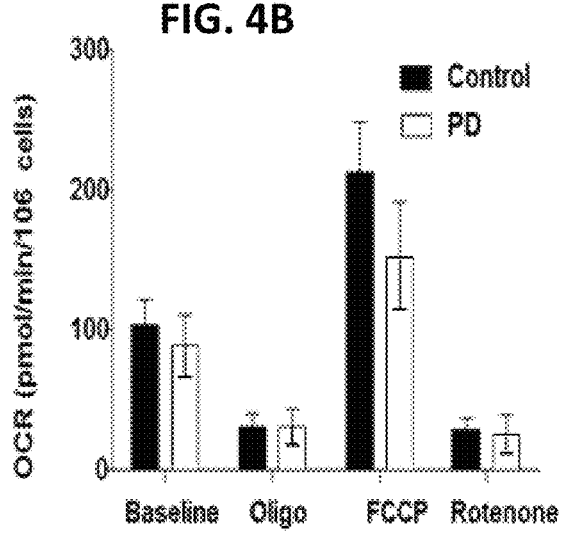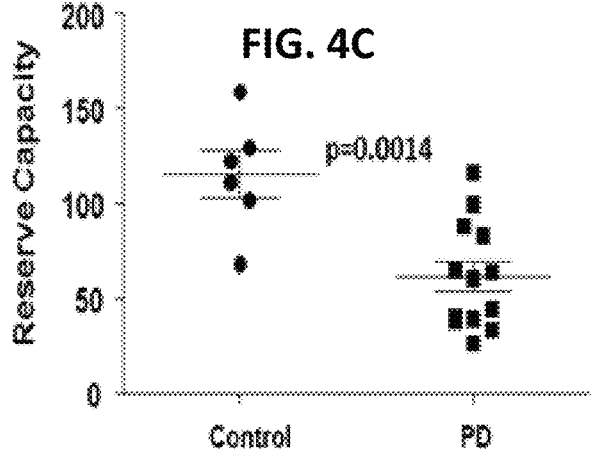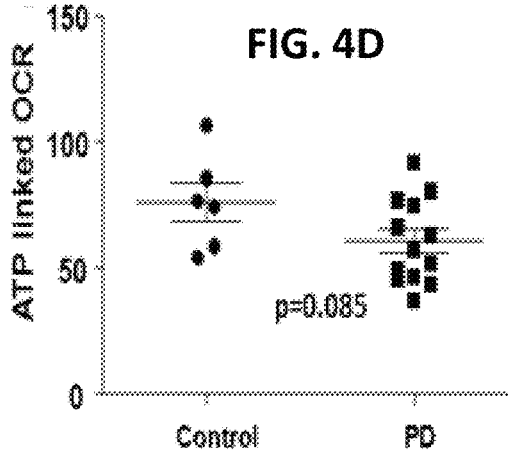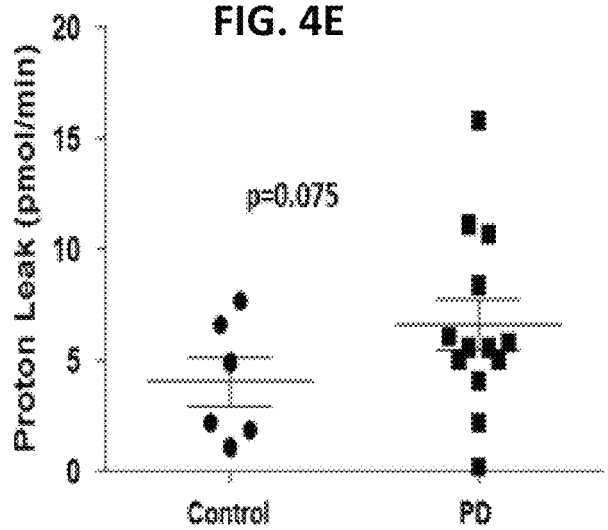

MITOCHONDRIAL HEALTH PARAMETERS AS CLINICAL PREDICTORS OF PARKINSON'S DISEASE

CROSS REFERENCE TO RELATED APPLICATIONS

This is a continuation of U.S. patent application Ser. No. 15/758,695, filed on Mar. 8, 2018, which is a § 371 U.S. national stage of International Application No. PCT/US2016/050773, filed Sep. 8, 2016, which claims the benefit of U.S. Provisional Application No. 62/216,199, filed Sep. 9, 2015, and U.S. Provisional Application No. 62/271,911, filed on Dec. 28, 2015, which are both incorporated by reference in their entirety.

ACKNOWLEDGMENT OF GOVERNMENT SUPPORT

This invention was made with government support under R01 ES020718 awarded by the National Institutes of Health. The government has certain rights in the invention.

FIELD

This relates to methods for detecting peripheral mitochondrial DNA damage and dysfunction, and provides diagnostic methods that utilize blood samples to detect a neurodegenerative disease, such as Parkinson's disease, and determine the efficacy of therapy.

BACKGROUND

Parkinson's disease (PD) is a devastating neurodegenerative movement disorder, pathologically characterized by the relatively selective loss of dopaminergic (DA) neurons in the substantia nigra pars *Compacta* (SNpc) and the presence of intracytoplasmic inclusions named Lewy bodies and Lewy neurites (Schapira, *Baillieres Clin. Neurol.* 6:15-36, 1997). Increasing numbers of genes have been identified as a genetic cause of PD (Hardy et al., Ann. Neurol. 60:389-398, 2006). For example, multiple missense mutations in the leucine-rich repeat kinase 2 (LRRK2) gene were recently found to be associated with an autosomal dominant form of familial PD (Paisan-Ruiz et al., *Neuron* 44:595-600, 2004; Zimprich et al., *Neuron* 44:601-607, 2004; Zabetian et al., *Neurology* 65:741-744, 2005). LRRK2 contains both functional kinase and GTPase enzymatic activities, as well as multiple protein interaction domains (Paisan-Ruiz et al., *Neuron* 44:595-600, 2004; Zimprich et al., *Neuron* 44:601-607, 2004; West et al., *Proc. Natd. Acad. Sci. U.S.A.* 102:16842-16847, 2005), which are likely involved in neuronal morphogenesis and maintenance, microtubule and actin dynamics, synaptic vesicle release, and other functions (West et al., *Proc. Nat. Acad. Sci. U.S.A.* 102:16842-16847, 2005; Li et al., *J. Neurochem.* 103(1):238-247, 2007). Despite years of research, there is no one test or technique that can provide a conclusive primary diagnosis of PD. The current diagnostic methods that are in use are based on medical history evaluation and a combination of physical and neurological assessments (Hughes et al. (2002) Brain: A Journal of Neurology 125:861-870; Gelb et al. (1999) Archives of Neurology 56:33-39). Standard practices for these assessments, such as the Unified Parkinson's Disease Rating Scale (UPDRS; Goetz et al. (2008) Movement Disorders 23:2129-2170) assist with the clinical staging of the disease, but fail to detect PD before the onset of initial motor symptoms.

Parkinson's disease affects around 1% to 2% of the population over 60 years of age, and is expected to increase in prevalence as the global population ages in the twenty-first century. Thus, a need remains for methods for identifying subjects that have Parkinson's disease, and for determining if a therapeutic treatment protocol is effective.

SUMMARY

Methods are disclosed for diagnosing a neurodegenerative disease, such as Parkinson's disease, for determining the severity, and for monitoring progression of the neurodegenerative disease, such as Parkinson's disease. In other embodiments, the methods can include determining whether a subject will respond to a specific therapeutic agent for the treatment of a neurodegenerative disease, such as Parkinson's disease, such as a specific formulation or dose of L-dopa. In yet other embodiments, these methods can be used to determine the lowest effective dosage of the therapeutic agent of use to treat the subject. The disclosed methods measure the lesion frequency in mitochondrial DNA.

In some embodiments, the method is non-invasive. In specific, non-limiting examples of any of the methods disclosed herein, the sample is a blood sample. In other embodiments of any of the methods disclosed herein, this sample can be a purified blood component, such as leukocytes or platelets. In further embodiments, the method utilizes polymerase chain reaction (PCR), such as quantitative PCR (qPCR).

The foregoing and other objects, features, and advantages of the invention will become more apparent from the following detailed description, which proceeds with reference to the accompanying figures.

BRIEF DESCRIPTION OF THE FIGURES

FIG. 1. Quantitative mtDNA damage assay: 96 well platform. A representative graph showing data obtained from a control (black) and Parkinson's disease (grey) sample.

FIGS. 4A-4E. PD patients have altered bioenergetics. (A) Representative bioenergetic profiles of platelets from PD patients and healthy controls. (B) Quantitation of traces similar to those shown in A. (C) Reserve capacity, (D) ATP linked OCR and (E) proton leak in control and PD platelets. N=6 control and 13 PD patients.

FIG. 5A demonstrates a significant (p=0.038) negative correlation between ATP linked respiration and SF-36 total score. FIG. 5B shows a significant correlation (p=0.039) between maximal respiratory capacity and MDS part 1 score.

SEQUENCE LISTING

Figure 2:
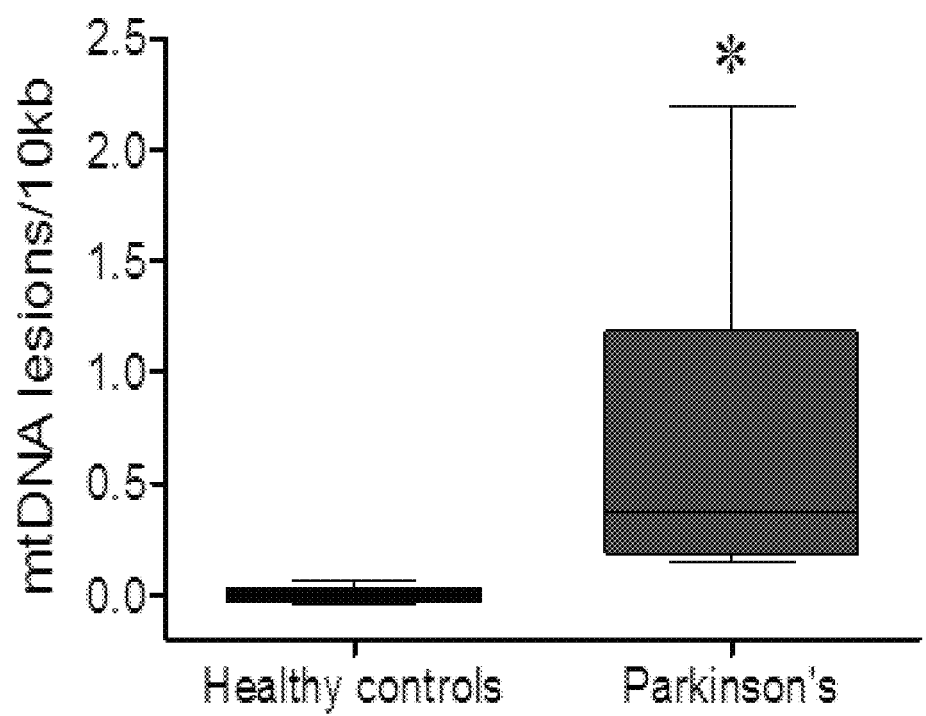
FIG. 2. Six age-matched controls and 14 Parkinson's Disease (PD) subjects were recruited for this study. Blood samples were collected and then subsequently buffy coat (platelets & leukocytes) DNA was purified. There was a statistically significant difference in the number of mitochondrial DNA lesions (per 10 kb).

The nucleic and amino acid sequences listed in the accompanying sequence listing are shown using standard letter abbreviations for nucleotide bases, and three letter code for amino acids, as defined in 37 C.F.R. 1.822. Only one strand of each nucleic acid sequence is shown, but the complementary strand is understood as included by any reference to the displayed strand where appropriate. The Sequence Listing is submitted as an ASCII text file [8123-95728-05_Sequence_Listing, Apr. 9, 2021, 1.05 KB], which is incorporated by reference herein.

SEQ ID NOs: 1-3 are primer sequences.

DETAILED DESCRIPTION

It is disclosed herein that mitochondrial DNA damage can be used in the diagnosis and prognosis of a neurodegenerative disease, such as Parkinson's disease or Parkinsonism. These assays can also be used to determine severity and progression of the disease. The assays disclosed herein can be used to monitor the course of therapy and/or the efficacy of treatments. In some embodiments, these methods can be used to determine the lowest effective dosage, or duration, of the therapeutic agent of use to treat the subject.

Mitochondrial DNA (mtDNA) damage assays are time- and labor-intensive. Previously, single tubes were used to perform a mtDNA damage assay using standard PCR machines. At best, to obtain data for six samples takes about a week, and more typically two to several weeks. Disclosed herein is an assay that can be used in a microplate-based format. Two barriers were overcome: (1) a dye that was compatible for real-time thermal cyclers that was sufficient for this assay was identified, and (2) an equation was developed that that enables us to calculation of the mtDNA lesion frequency. In addition, PCR conditions were optimized.

Without limitation, there are advantages to this newly adapted multi-well mtDNA damage assay: 1) it can be used in high throughput format; 2) it is sensitive, consistent and reliable; 3) it is quick, and has reduced assays times from weeks to days; 4) it is low cost and easily adaptable to other platforms, such as a 396-well platform.

The methods disclosed herein can be used for screening and translational human studies.

Terms

Unless otherwise noted, technical terms are used according to conventional usage. Definitions of common terms in molecular biology may be found in Benjamin Lewin, Genes V, published by Oxford University Press, 1994 (ISBN 0-19-854287-9); Kendrew et al. (eds.), The *Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 1-56081-569-8).

In order to facilitate review of the various embodiments of the disclosure, the following explanations of specific terms are provided:

3' end: The end of a nucleic acid molecule that does not have a nucleotide bound to it 3' of the terminal residue.

5' end: The end of a nucleic acid sequence where the 5' position of the terminal residue is not bound by a nucleotide.

Administration: To provide or give a subject an agent, such as a therapeutic agent, by any effective route. Exemplary routes of administration include, but are not limited to, injection (such as subcutaneous, intramuscular, intradermal, intraperitoneal, and intravenous), oral, intraductal, sublingual, rectal, transdermal, intranasal, vaginal and inhalation routes.

Agent: Any protein, nucleic acid molecule (including chemically modified nucleic acids), compound, small molecule, organic compound, inorganic compound, or other molecule of interest. "Agent" can include a therapeutic agent, a diagnostic agent or a pharmaceutical agent. A therapeutic or pharmaceutical agent is one that alone or together with an additional compound induces the desired response (such as inducing a therapeutic or prophylactic effect when administered to a subject).

Alkyl: A hydrocarbon group having a saturated carbon chain. The chain may be cyclic, branched or unbranched. The term lower alkyl means the chain includes 1-10 carbon atoms. The terms alkenyl and alkynyl refer to hydrocarbon groups having carbon chains containing one or more double or triple bonds, respectively.

Alkylamino: A chemical functional group —N(H)R, where R is an alkyl group.

Amino: A chemical functional group —N(R)R' where R and R' are independently hydrogen, alkyl, heteroalkyl, haloalkyl, aliphatic, heteroaliphatic, aryl (such as optionally substituted phenyl or benzyl), heteroaryl, alkylsulfano, or other functionality. A "primary amino" group is —NH$_2$. "Mono-substituted amino" means a radical—N(H)R substituted as above and includes, e.g., methylamino, (1-methylethyl)amino, phenylamino, and the like. "Di-substituted amino" means a radical—N(R)R' substituted as above and includes, e.g., dimethylamino, methylethylamino, di(1-methylethyl)amino, and the like.

Amplification: A technique that increases the number of copies of a nucleic acid molecule (such as an RNA or DNA). An example of amplification is polymerase chain reaction (PCR), in which a sample is contacted with a pair of oligonucleotide primers under conditions that allow for the hybridization of the primers to a nucleic acid template in the sample. The primers are extended under suitable conditions, dissociated from the template, re-annealed, extended, and dissociated to amplify the number of copies of the nucleic acid. The product of amplification can be characterized by electrophoresis, restriction endonuclease cleavage patterns, oligonucleotide hybridization or ligation, and/or nucleic acid sequencing using standard techniques. The reaction product can be quantified.

Other examples of amplification include quantitative real-time polymerase chain reaction (qPCR), strand displacement amplification, as disclosed in U.S. Pat. No. 5,744,311; transcription-free isothermal amplification, as disclosed in U.S. Pat. No. 6,033,881; repair chain reaction amplification, as disclosed in PCT publication WO 90/01069; ligase chain reaction amplification, as disclosed in European patent publication EP-A-320,308; gap filling ligase chain reaction amplification, as disclosed in U.S. Pat. No. 5,427,930; and NASBA RNA transcription-free amplification, as disclosed in U.S. Pat. No. 6,025,134. Several embodiments include multiplex qPCR assays, which are useful for amplifying and detecting multiple nucleic acid sequences in a single reaction.

Biological sample: A sample of biological material obtained from a subject. Biological samples include all clinical samples useful for detection of disease (such as Parkinson's disease) in subjects. Appropriate samples include any conventional biological samples, including clinical samples obtained from a human or veterinary subject. Exemplary samples include, without limitation, cells, cell lysates, blood samples, white blood cell samples, plasma samples, leukocytes and platelets. In a particular example, a biological sample is obtained from a subject having, suspected of having or at risk of having, Parkinson's disease.

Conservative variant: A "conservative variant" of a probe or primer includes sequences that have altered nucleic acid sequences, but retain their ability to bind to the target sequences (and identify or amplify the target sequence) with sufficient specificity. In some particular examples, no more than about 1, 2, 5, or 10 nucleic acids are changed, or the probe or primer retains at least 80%, 85%, 90%, or 95% sequence identity to the original sequence. Conservative variants also include probe or primer sequences to which additional sequence has been added, while still retaining the noted specificity of the probe or primer.

Consists of or consists essentially of: With regard to a polynucleotide (such as a probe or primer), a polynucleotide consists essentially of a specified nucleotide sequence if it does not include any additional nucleotides. However, the polynucleotide can include additional non-nucleic acid components, such as labels (for example, fluorescent, radioactive, or solid particle labels), sugars or lipids. With regard to a polynucleotide, a polynucleotide that consists of a specified nucleotide sequence does not include any additional nucleotides, nor does it include additional non-nucleic acid components, such as lipids, sugars or labels.

Contacting: Placement in direct physical association, for example solid, liquid or gaseous forms. Contacting includes, for example, direct physical association of fully- and partially-solvated molecules.

Control: A "control" refers to a sample or standard used for comparison with an experimental sample, such as a sample obtained from a patient with Parkinson's disease. In some embodiments, the control is a sample obtained from a healthy patient (which in the context of the present disclosure includes any subject that does not have Parkinson's disease). In some embodiments, the control is a historical control or standard value (i.e. a previously tested control sample or group of samples that represent baseline or normal values). In other embodiments, the control is a sample obtained from a patient with Parkinson's disease prior to a particular treatment (such as to compare with a sample obtained after treatment). Similarly, when evaluating a candidate agent in a cell culture, a control also includes cells that have not been treated with the candidate agent.

Detectable marker: A detectable molecule (also known as a label) that is conjugated directly or indirectly to a second molecule, such as a nucleic acid molecule, to facilitate detection of the second molecule. The person of ordinary skill in the art is familiar with detectable markers for labeling nucleic acid molecules and their use. For example, the detectable marker can be capable of detection by ELISA, spectrophotometry, flow cytometry, or microscopy. Specific, non-limiting examples of detectable markers include fluorophores, fluorescent proteins, chemiluminescent agents, enzymatic linkages, radioactive isotopes and heavy metals or compounds. In several embodiments, the detectable markers are designed for use with qPCR, such as multiplex qPCR. Various methods of labeling nucleic acid molecules are known in the art and may be used.

Detecting: To identify the existence, presence, or fact of something. General methods of detecting are known to the skilled artisan and may be supplemented with the protocols and reagents disclosed herein. For example, included herein are methods of detecting peripheral mitochondrial DNA damage and dysfunction. Detection can include a physical readout, such as fluorescence or a reaction output.

Diagnosis: The process of identifying a disease, such as Parkinson's disease by its signs, symptoms and/or results of tests. The conclusion reached through that process is also called "a diagnosis." Forms of testing commonly performed include physical exam, blood tests, medical imaging, genetic analysis, urinalysis, and biopsy. Testing also includes the use of molecular techniques, such as PCR.

Healthy control subject: A subject that is not clinically diagnosed with Parkinson's disease after an appropriate examination.

Halogen: Any of the elements fluorine, chlorine, bromine, iodine, and astatine, occupying group VIIA (17) of the periodic table. They are reactive nonmetallic elements that form strongly acidic compounds with hydrogen, from which simple salts can be made. A halogen forms binary salts by direct union with metals.

Hybridization: The terms "annealing" and "hybridization" refer to the formation of base pairs between complementary regions of DNA, RNA, or between DNA and RNA of nucleic acids. Examples of annealing and hybridization include formation of base pairs between two separate nucleic acid molecules, as well as formation of base pairs between nucleic acids on a single nucleic acid molecule.

In some examples, hybridization is between two complementary nucleic acid sequences, for example nucleic acid sequences that are at least 90% complementary to each other, such as at least 91%, 92%, 93%, 94%, 95%, 96%, 97%, 98%, 99%, or 100% complementary to each other.

In additional embodiments, hybridization conditions resulting in particular degrees of stringency and specificity will vary depending upon the nature of the hybridization method and the composition and length of the hybridizing nucleic acid sequences. Generally, the temperature of hybridization and the ionic strength (such as the $Na^+$ concentration) of the hybridization buffer will determine the stringency of hybridization. Calculations regarding hybridization conditions for attaining particular degrees of stringency are discussed in Sambrook et al., (1989) Molecular Cloning, second edition, Cold Spring Harbor Laboratory, Plainview, N.Y. (chapters 9 and 11). The following is an exemplary set of hybridization conditions and is not limiting:

Very High Stringency (detects sequences that share at least 90% identity)
    Hybridization: 5×SSC at 65° C. for 16 hours
    Wash twice: 2×SSC at room temperature (RT) for 15 minutes each
    Wash twice: 0.5×SSC at 65° C. for 20 minutes each High Stringency (detects sequences that share at least 80% identity)
    Hybridization: 5×-6×SSC at 65° C.-70° C. for 16-20 hours
    Wash twice: 2×SSC at RT for 5-20 minutes each
    Wash twice: 1×SSC at 55° C.-70° C. for 30 minutes each Low Stringency (detects sequences that share at least 50% identity)
    Hybridization: 6×SSC at RT to 55° C. for 16-20 hours
    Wash at least twice: 2×-3×SSC at RT to 55° C. for 20-30 minutes each In some embodiments, the probes and primers disclosed herein can hybridize to nucleic acid molecules under low stringency, high stringency, and very high stringency conditions.

Isolated: An "isolated" biological component (such as a nucleic acid molecule, protein, or cell) has been substantially separated or purified away from other biological components in the cell or tissue of the organism, or the organism itself, in which the component naturally occurs, such as other chromosomal and extra-chromosomal DNA and RNA, proteins and cells. Nucleic acid molecules and proteins that have been "isolated" include those purified by standard purification methods. The term also embraces nucleic acid molecules and proteins prepared by recombinant expression in a host cell as well as chemically synthesized nucleic acid molecules and proteins.

L-DOPA: L-3,4-dihydroxyphenylalanine. L-DOPA is the precursor to the neurotransmitters dopamine, norepinephrine (noradrenaline), and epinephrine (adrenaline) collectively known as catecholamines. L-DOPA mediates neurotrophic factor release by the brain and CNS. L-DOPA is sold as a psychoactive drug with the INN levodopa; trade names include SINEMET®, PARCOPA®, ATAMET®, STALEVO®, MADOPAR®, and PROLOPA®. L-DOPA is used in the clinical treatment of Parkinson's disease.

Label: A detectable molecule that is conjugated directly or indirectly to a second molecule, such as a nucleic acid molecule, to facilitate detection of the second molecule. The person of ordinary skill in the art is familiar with detectable markers for labeling nucleic acid molecules and their use. In some examples, the detectable marker can be capable of detection by ELISA, spectrophotometry, flow cytometry, or microscopy. Specific, non-limiting examples of detectable markers include fluorophores, fluorescent proteins, chemiluminescent agents, enzymatic linkages, radioactive isotopes and heavy metals or compounds. In several embodiments, the detectable markers are designed for use with qPCR, such as multiplex qPCR. Various methods of labeling nucleic acid molecules are known in the art and may be used. A "unique" label is a label that is distinct from others in a reaction, such that the identity of a single bound molecule can be known when the label is detected.

Mitochondrion: A double membrane-bound organelle found in most eukaryotic cells that ranges in size from 0.5 to 1.0 μm in diameter. Mitochondria generate most of the cell's supply of adenosine triphosphate (ATP. In addition to supplying cellular energy, mitochondria are involved in other tasks, such as signaling, cellular differentiation, and cell death, as well as maintaining control of the cell cycle and cell growth. A mitochondrion has its own genome, independent from the cellular genome in the nucleus.

Multiplex qPCR: Amplification and detection of more than one nucleic acid sequence in a single qPCR reaction. By multiplexing, target nucleic acids can be amplified in single tube. In some examples, multiplex PCR permits the simultaneous detection of the amplification products of a region of a gene of interest using the disclosed probes.

Nucleic acid: A polymer composed of nucleotide units (ribonucleotides, deoxyribonucleotides, related naturally occurring structural variants, and synthetic non-naturally occurring analogs thereof) linked via phosphodiester bonds, related naturally occurring structural variants, and synthetic non-naturally occurring analogs thereof. Thus, the term includes nucleotide polymers in which the nucleotides and the linkages between them include non-naturally occurring synthetic analogs, such as, for example and without limitation, phosphorothioates, phosphoramidates, methyl phosphonates, chiral-methyl phosphonates, 2-O-methyl ribonucleotides, peptide-nucleic acids (PNAs), and the like. Such polynucleotides can be synthesized, for example, using an automated DNA synthesizer. It will be understood that when a nucleotide sequence is represented by a DNA sequence (i.e., A, T, G, C), this also includes an RNA sequence (i.e., A, U, G, C) in which "U" replaces "T."

"Nucleotide" includes, but is not limited to, a monomer that includes a base linked to a sugar, such as a pyrimidine, purine or synthetic analogs thereof, or a base linked to an amino acid, as in a peptide nucleic acid (PNA). A nucleotide is one monomer in a polynucleotide. A nucleotide sequence refers to the sequence of bases in a polynucleotide.

Conventional notation is used herein to describe nucleotide sequences: the left-hand end of a single-stranded nucleotide sequence is the 5'-end; the left-hand direction of a double-stranded nucleotide sequence is referred to as the 5'-direction. The direction of 5' to 3' addition of nucleotides to nascent RNA transcripts is referred to as the transcription direction. The DNA strand having the same sequence as an mRNA is referred to as the "coding strand;" sequences on the DNA strand having the same sequence as an mRNA transcribed from that DNA and which are located 5' to the 5'-end of the RNA transcript are referred to as "upstream sequences;" sequences on the DNA strand having the same sequence as the RNA and which are 3' to the 3' end of the coding RNA transcript are referred to as "downstream sequences."

"cDNA" refers to a DNA that is complementary or identical to an mRNA, in either single stranded or double stranded form.

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (for example, rRNA, tRNA and mRNA) or a defined sequence of amino acids and the biological properties resulting therefrom. Thus, a gene encodes a protein if transcription and translation of mRNA produced by that gene produces the protein in a cell or other biological system. Both the coding strand, the nucleotide sequence of which is identical to the mRNA sequence and is usually provided in sequence listings, and non-coding strand, used as the template for transcription, of a gene or cDNA can be referred to as encoding the protein or other product of that gene or cDNA. Unless otherwise specified, a "nucleotide sequence encoding an amino acid sequence" includes all nucleotide sequences that are degenerate versions of each other and that encode the same amino acid sequence. Nucleotide sequences that encode proteins and RNA may include introns. In some examples, a nucleic acid encodes a disclosed antigen.

Oligonucleotide probes and primers: A probe includes an isolated nucleic acid (usually of 100 or fewer nucleotide residues), that can be attached to a detectable label or reporter molecule, which is used to detect a complementary target nucleic acid molecule by hybridization and detection of the label or reporter. Isolated oligonucleotide probes (which as defined herein also include the complementary sequence and corresponding RNA sequences) are of use for detection a particular nucleic acid. Typically, probes are at least about 10 nucleotides in length, such as at least about 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or about 100 nucleotides in length. For example, a probe can be about 10-100 nucleotides in length, such as, 12-15, 12-20, 12-25, 12-30, 12-35, 12-40, 12-45, 12-50, 12-80, 14-15, 14-16, 14-18, 14-20, 14-25, 14-30, 15-16, 15-18, 15-20, 15-25, 15-30, 15-35, 15-40, 15-45, 15-50, 15-80, 16-17, 16-18, 16-20, 16-22, 16-25, 16-30, 16-40, 16-50, 17-18, 17-20, 17-22, 17-25, 17-30, 18-19, 18-20, 18-22, 18-25, 18-30, 19-20, 19-22, 19-25, 19-30, 20-21, 20-22, 20-25, 20-30, 20-35, 20-40, 20-45, 20-50, 20-80, 21-22, 21-25, 21-30, 22-25, 22-30, 22-40, 22-50, 23-24, 23-25, 23-30, 24-25, 24-30, 25-35, 25-30, 25-35, 25-40, 25-45, 25-50 or 25-80 nucleotides in length.

Primers are nucleic acid molecules, usually DNA oligonucleotides of about 10-50 nucleotides in length (longer lengths are also possible). Typically, primers are at least about 10 nucleotides in length, such as at least about 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or about 50 nucleotides in length. For example, a primer can be about 10-50 nucleotides in length, such as, 12-15, 12-20, 12-25, 12-30, 12-35, 12-40, 12-45, 12-50, 14-15, 14-16, 14-18, 14-20, 14-25, 14-30, 15-16, 15-18, 15-20, 15-25, 15-30, 15-35, 15-40, 15-45, 15-50, 16-17, 16-18, 16-20, 16-22, 16-25, 16-30, 16-40, 16-50, 17-18, 17-20, 17-22, 17-25, 17-30, 18-19, 18-20, 18-22, 18-25, 18-30, 19-20, 19-22, 19-25, 19-30, 20-21, 20-22, 20-25, 20-30, 20-35, 20-40, 20-45, 20-50, 21-22, 21-25, 21-30, 22-25, 22-30, 22-40, 22-50, 23-24, 23-25, 23-30, 24-25, 24-30, 25-30, 25-35, 25-40 or 25-45, 25-50 nucleotides in length.

Probes and primers can also be of a maximum length, for example no more than 15, 25, 25, 40, 50, 75 or 100 nucleotides in length.

Primers may be annealed to a complementary target DNA strand by nucleic acid hybridization to form a hybrid between the primer and the target DNA strand, and then extended along the target DNA strand by a DNA polymerase enzyme. One of skill in the art will appreciate that the hybridization specificity of a particular probe or primer typically increases with its length. Thus, for example, a probe or primer including 20 consecutive nucleotides typically will anneal to a target with a higher specificity than a corresponding probe or primer of only 15 nucleotides. In some embodiments, probes and primers are used in combination in a quantitative PCR reaction.

Operably linked: A first molecule, such as a nucleic acid or protein, is operably linked with a second molecule when the first molecule is placed in a functional relationship with the second molecule. For instance, a promoter is operably linked to a nucleic acid coding sequence if the promoter affects the transcription or expression of the coding sequence. Additionally, an intron is operably linked to an exon for the function of splicing. Generally, operably linked nucleotide sequences are contiguous.

Parkinson's disease: A degenerative disorder of the central nervous system that impairs motor skills, cognitive processes, and other functions. Parkinson's disease is also referred to as Parkinson's disease, Parkinson's, PD and primary parkinsonism. The most obvious symptoms of Parkinson's disease are motor-related, including tremor, rigidity, slowness of movement and postural instability. Among non-motor symptoms are autonomic dysfunction and sensory and sleep difficulties. Cognitive and neurobehavioral problems, including dementia, are common in the advanced stages of the disease.

In subjects that develop Parkinson's disease, symptoms typically begin around the age of 60, although there are young-onset cases. Symptoms result from insufficient formation and action of dopamine produced in the dopaminergic neurons of the midbrain (specifically the substantia nigra). Pathologically the disease is characterized by the accumulation of alpha-synuclein protein forming inclusions called Lewy bodies. Such pathology can only be demonstrated at autopsy so diagnosis is mainly clinical (based on symptoms). Some tests such as neuroimaging techniques can also aid in diagnosis.

Current treatments are effective at managing the early motor symptoms of the disease, through the use of levodopa, dopamine agonists and MAO-B inhibitors. As the disease advances, however, the continued use of medications leads to a second stage in which the patient develops motor complications called dyskinesias. Medications to treat other symptoms of PD also exist. Diet and some forms of rehabilitation have shown some effectiveness at mitigating symptoms, and surgery and deep brain stimulation may be used to reduce motor symptoms in the most extreme cases.

Patient: As used herein, the term "patient" includes human and non-human animals. The preferred patient for treatment is a human. "Patient" and "subject" are used interchangeably herein.

Pharmaceutically acceptable vehicles: The pharmaceutically acceptable carriers (vehicles) useful in this disclosure are conventional. Remington's Pharmaceutical Sciences, by E. W. Martin, Mack Publishing Co., Easton, Pa., 15th Edition (1975), describes compositions and formulations suitable for pharmaceutical delivery of one or more therapeutic compounds, molecules or agents.

In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (for example, powder, pill, tablet, or capsule forms), conventional non-toxic solid carriers can include, for example, pharmaceutical grades of mannitol, lactose, starch, or magnesium stearate. In addition to biologically-neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

Phenyl: A cyclic group of atoms with the formula $C_6H_5$, often represented by the symbol "Ph." Phenyl groups are closely related to benzene. Phenyl groups have six carbon atoms bonded together in a hexagonal planar ring, five of which are bonded to individual hydrogen atoms, with the remaining carbon bonded to a substituent.

Preventing, treating or ameliorating a disease: "Preventing" a disease (such as Parkinson's disease) refers to inhibiting the full development of a disease. "Treating" refers to a therapeutic intervention that ameliorates a sign or symptom of a disease or pathological condition after it has begun to develop. "Ameliorating" refers to the reduction in the number or severity of signs or symptoms of a disease.

Quantitative real-time PCR (qPCR): A method for detecting and measuring products generated during each cycle of a PCR, which are proportionate to the amount of template nucleic acid prior to the start of PCR. The information obtained, such as an amplification curve, can be used to determine the presence of a target nucleic acid and/or quantitate the initial amounts of a target nucleic acid sequence. Exemplary procedures for real-time PCR can be found in "Quantitation of DNA/RNA Using Real-Time PCR Detection" published by Perkin Elmer Applied Biosystems (1999); *PCR Protocols* (Academic Press, New York, 1989);

A-Z of *Quantitative* PCR, Bustin (ed.), International University Line, La Jolla, Calif., 2004; and *Quantitative Real-Time PCR in Applied Microbiology*, Filion (Ed), Caister Academic Press, 2012.

In some examples, the amount of amplified target nucleic acid is detected using a labeled probe, such as a probe labeled with a fluorophore. In this example, the increase in fluorescence emission is measured in real-time, during the course of the real-time PCR. This increase in fluorescence emission is directly related to the increase in target nucleic acid amplification. In some examples, the change in fluorescence (Delta Rn; dRn; $\Delta$Rn) is calculated using the equation $dRn=Rn^+-Rn^-$, with $Rn^+$ being the fluorescence emission of the product at each time point and Rn-being the fluorescence emission of the baseline. The dRn values are plotted against cycle number, resulting in amplification plots for each sample. The threshold value ($C_t$) is the PCR cycle number at which the fluorescence emission (dRn) exceeds a chosen threshold, which is typically 10 times the standard deviation of the baseline (this threshold level can, however, be changed if desired).

The threshold cycle is when the system begins to detect the increase in the signal associated with an exponential growth of PCR product during the log-linear phase. This phase provides information about the reaction. The slope of the log-linear phase is a reflection of the amplification efficiency. The efficiency of the reaction can be calculated by the following equation: $E=10^{(-1/slope)}$, for example. The efficiency of the PCR should be 90-100% meaning doubling of the amplicon at each cycle. This corresponds to a slope of −3.1 to −3.6 in the $C_t$ vs. log-template amount standard curve.

Recombinant: A recombinant nucleic acid molecule is one that has a sequence that is not naturally occurring or has a sequence that is made by an artificial combination of two otherwise separated segments of sequence. This artificial combination can be accomplished by chemical synthesis or by the artificial manipulation of isolated segments of nucleic acid molecules, such as by genetic engineering techniques.

Sample: A specimen containing genomic DNA, RNA (such as mRNA or microRNA), protein, cells, tissues or combinations thereof, obtained from a subject. Examples include, but are not limited to, saliva, peripheral blood, urine, tissue biopsy, surgical specimen, and autopsy material. In some embodiments, the sample is blood, or a component thereof, such as plasma or serum. In some cases, a sample is obtained from a patient with Parkinson's disease or a healthy subject, such as a blood or plasma sample, or isolated blood cells.

Sensitivity and specificity: Statistical measurements of the performance of a binary classification test. Sensitivity measures the proportion of actual positives which are correctly identified (e.g., the percentage of samples that are identified as including nucleic acid from a particular pathogen). Specificity measures the proportion of negatives which are correctly identified (e.g., the percentage of samples that are identified as not including nucleic acid from a particular pathogen).

Sequence identity: The similarity between two nucleic acid sequences, is expressed in terms of the similarity between the sequences, otherwise referred to as sequence identity. Sequence identity is frequently measured in terms of percentage identity, similarity, or homology; a higher percentage identity indicates a higher degree of sequence similarity.

The NCBI Basic Local Alignment Search Tool (BLAST), Altschul et al., *J. Mol. Biol.* 215:403-10, 1990, is available from several sources, including the National Center for Biotechnology Information (NCBI, Bethesda, Md.), for use in connection with the sequence analysis programs blastp, blastn, blastx, tblastn and tblastx. It can be accessed through the NCBI website. A description of how to determine sequence identity using this program is also available on the website.

When less than the entire sequence is being compared for sequence identity, homologs will typically possess at least 75% sequence identity over short windows of 10-20 amino acids, and can possess sequence identities of at least 85% or at least 90% or 95% depending on their similarity to the reference sequence. Methods for determining sequence identity over such short windows are described on the NCBI website.

These sequence identity ranges are provided for guidance only; it is entirely possible that strongly significant homologs could be obtained that fall outside of the ranges provided.

An alternative indication that two nucleic acid molecules are closely related is that the two molecules hybridize to each other under stringent conditions. Stringent conditions are sequence-dependent and are different under different environmental parameters. Generally, stringent conditions are selected to be about 5° C. to 20° C. lower than the thermal melting point (Tm) for the specific sequence at a defined ionic strength and pH. The Tm is the temperature (under defined ionic strength and pH) at which 50% of the target sequence hybridizes to a perfectly matched probe. Conditions for nucleic acid hybridization and calculation of stringencies can be found in Sambrook et al.; and Tijssen, *Hybridization With Nucleic Acid Probes, Part I: Theory and Nucleic Acid Preparation*, Laboratory Techniques in Biochemistry and Molecular Biology, Elsevier Science Ltd., 1993.

Signal: A detectable change or impulse in a physical property that provides information. In the context of the disclosed methods, examples include electromagnetic signals such as light, for example light of a particular quantity or wavelength. In certain examples, the signal is the disappearance of a physical event, such as quenching of light.

Specifically binds: A nucleic acid sequence that, under a defined set of reaction conditions, binds to its complement and not to other nucleic acid sequences. A probe that specifically binds to its target can be used in RT-PCR assays. Generally a probe that specifically binds can be used to distinguish that nucleic acid sequence from other nucleic acids.

Sequence identity/similarity: The identity/similarity between two or more nucleic acid sequences, or two or more amino acid sequences, is expressed in terms of the identity or similarity between the sequences. Sequence identity can be measured in terms of percentage identity; the higher the percentage, the more identical the sequences are. Sequence similarity can be measured in terms of percentage similarity (which takes into account conservative amino acid substitutions); the higher the percentage, the more similar the sequences are. Homologs or orthologs of nucleic acid or amino acid sequences possess a relatively high degree of sequence identity/similarity when aligned using standard methods. This homology is more significant when the orthologous proteins or cDNAs are derived from species which are more closely related (such as human and mouse sequences), compared to species more distantly related (such as human and *C. elegans* sequences).

Methods of alignment of sequences for comparison are well known in the art. Various programs and alignment algorithms are described in: Smith & Waterman, *Adv. Appl. Math.* 2:482, 1981; Needleman & Wunsch, *J. Mol. Biol.* 48:443, 1970; Pearson & Lipman, *Proc. Natl. Acad. Sci. USA* 85:2444, 1988; Higgins & Sharp, *Gene,* 73:237-44, 1988; Higgins & Sharp, CABIOS 5:151-3, 1989; Corpet et al., *Nuc. Acids Res.* 16:10881-90, 1988; Huang et al. *Computer Appls. in the Biosciences* 8, 155-65, 1992; and Pearson et al., *Meth. Mol. Bio.* 24:307-31, 1994. Altschul et al., *J. Mol. Biol.* 215:403-10, 1990, presents a detailed consideration of sequence alignment methods and homology calculations.

The NCBI Basic Local Alignment Search Tool (BLAST) (Altschul et al., *J. Mol. Biol.* 215:403-10, 1990) is available from several sources, including the National Center for Biological Information (NCBI) and on the internet, for use in connection with the sequence analysis programs blastp, blastn, blastx, tblastn and tblastx. Additional information can be found at the NCBI web site.

Subject: Living multi-cellular vertebrate organisms, a category that includes human and non-human mammals.

Target nucleic acid molecule: A nucleic acid molecule whose detection, quantitation, qualitative detection, or a combination thereof, is intended. The nucleic acid molecule need not be in a purified form. Various other nucleic acid molecules can also be present with the target nucleic acid molecule. For example, the target nucleic acid molecule can be a specific nucleic acid molecule (which can include RNA or DNA), the amplification of which is intended. Purification or isolation of the target nucleic acid molecule, if needed, can be conducted by methods known to those in the art, such as by using a commercially available purification kit or the like.

Therapeutic agent: A chemical compound, small molecule, or other composition, such as an antisense compound, microRNA, antibody, protease inhibitor, hormone, chemokine or cytokine, capable of inducing a desired therapeutic or prophylactic effect when properly administered to a subject.

Under conditions sufficient for: A phrase that is used to describe any environment that permits a desired activity. In one example the desired activity is amplification of a nucleic acid molecule.

Unless otherwise explained, all technical and scientific terms used herein have the same meaning as commonly understood by one of ordinary skill in the art to which this disclosure belongs. The singular terms "a," "an," and "the" include plural referents unless context clearly indicates otherwise. Similarly, "A or B" is intended to include "A," "B," and "both A and B," unless the context clearly indicates otherwise. It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of this disclosure, suitable methods and materials are described below. The term "comprises" means "includes." "About," when referring to nucleic acids, means within 5 nucleotides, such as a difference of 5, 4, 3, 2, or 1 nucleotide. All publications, patent applications, patents, and other references mentioned herein are incorporated by reference in their entirety. In case of conflict, the present specification, including explanations of terms, will control. In addition, the materials, methods, and examples are illustrative only and not intended to be limiting.

Overview of Diagnostic and Therapeutic Methods

Methods are disclosed herein for diagnosing a neurodegenerative disease, such as Parkinson's disease or Parkinsonism. The methods including confirming a diagnosis of the neurodegenerative disease, such as Parkinson's disease or Parkinsonism, such as a clinical diagnosis. These methods include obtaining a biological sample from a subject of interest, such as a subject suspected of having the neurodegenerative disease, such as Parkinson's disease or Parkinsonism, and performing a quantitative PCR reaction on a sample from the subject, as disclosed herein. The sample can be any sample of interest, including, but not limited to, a buffy coat or a peripheral blood sample. The sample can be white blood cells or platelets. In some embodiments, the methods including detecting an increased lesion frequency in mitochondrial DNA as compared to a control, wherein the increased lesion frequency indicates that the subject has Parkinson's disease.

In some embodiments, methods are disclosed for diagnosing the neurodegenerative disease, such as Parkinson's disease or Parkinsonism, that include contacting a biological sample comprising mitochondrial DNA from a subject of interest with a first forward primer comprising the nucleic acid sequence set forth as SEQ ID NO: 1, and a reverse primer comprising the nucleic acid sequence set forth as SEQ ID NO: 2. This first forward primer and the reverse primer amplify a large mitochondrial DNA product of 8900 nucleotides in length when there are no lesions in mitochondrial DNA.

In some embodiments, the methods also include contacting the sample with a second forward primer comprising the nucleic acid sequence set forth as SEQ ID NO: 3, wherein the second forward primer and the reverse primer amplify a short mitochondrial DNA product of 298 nucleotides in length. The reaction can be in the same container or in a different container. In some embodiments, it is in the same container. This can serve as an internal control.

The subject can be elderly, such as greater than 60, 65, 70, 75, 80, 85 or 90 years of age.

The mitochondrial DNA is amplified in a quantitative polymerase chain reaction comprising a fluorescent dye. Exemplary quantitative PCR reaction conditions, and exemplary fluorescent dyes are disclosed below. In some non-limiting examples, the fluorescent dye has the formula

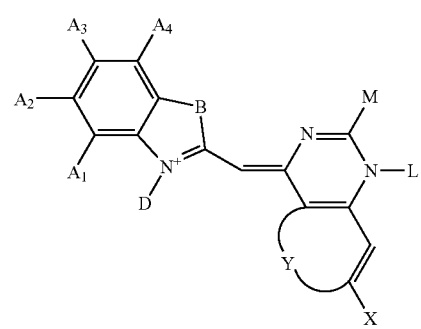

wherein all of $A_1$, $A_2$, $A_3$, and $A_4$ are H or one of $A_1$, $A_2$, $A_3$, and $A_4$ is a halogenyl and the others are H:

B is selected from the group consisting of S, O, N—R, and C—(R)$_2$ wherein R is $C_1$-$C_6$ alkyl;

D is an unsubstituted or substituted $C_1$-$C_6$ alkyl;

X is H or a methoxy group;

Y is selected from the group consisting of S, O, N—R wherein R is $C_1$-$C_6$ alkyl, and Z1-C═C—Z2 wherein Z1 and Z2 independently are H or a methoxy group;

L is CH$_3$ or phenyl; and

M is phenyl or a substituted or unsubstituted C$_1$-C$_{18}$ amino-alkyl.

Any of the alternative fluorescent dyes disclosed below can be used in these methods. In some embodiments, the quantitative PCR is performed for 40 cycles or less. The fluorescent dye is bound to the large DNA product during amplification, and the amount of the fluorescence emitted by the large DNA product at multiple points during the quantitative PCR reaction is determined, in order to establish the linear emission range for the biological sample. A determination is made of the lesion frequency of mitochondrial DNA in the biological sample in the linear emission range. Methods for this determination are disclosed below. An increase in the lesion frequency, as measured by a decrease in the amount of the large mitochondrial DNA product, specifically a decrease in the fluorescence from the large mitochondrial DNA product in the linear emission range, as compared to a control lesion frequency in a control linear emission range indicates that the subject has the neurodegenerative disease, such as Parkinson's disease or Parkinsonism.

In a quantitative PCR reaction, increased lesion frequency in mitochondrial DNA can be a shift in the linear portion of a graph of the number of cycles versus fluorescence. A decrease in fluorescence at a specific cycle within the linear range indicates that the subject has Parkinson's disease. Thus, the lesion frequency is compared to the lesion frequency in mitochondrial DNA in a control sample, such as a sample form a healthy subject that does not have the neurodegenerative disease, such as Parkinson's disease or Parkinsonism, or a standard value or curve.

In some embodiments, the methods also include administering to the subject a therapeutic agent for the treatment of Parkinson's disease. The therapeutic agent can be, for example, carbidopa and/or levodopa (L-dopa). The agent can be a domamine agoinst such as pramipexole (Mirapex), ropinirole (Requip) and rotigotine (given as a patch, Neupro). The agent can be a monoamine oxidase (MAO-B) inhibitor, such as selegiline (Eldepryl, Zelapar) and rasagiline (Azilect). The agent can be a catechol-O-methyltransferase inhibitor, such as entacapone (Comtan) or tocapone (Tasmar). In other embodiments, the agent is an anticholinergic such as benztropine (Cogentin) or trihexyphenidyl. The agent can be amantadine.

The methods disclosed herein also can include performing a bioenergetics assay on a white blood cell or a platelet sample from the subject. Suitable assays are known in the art, and exemplary assays are disclosed below. In specific, non-limiting examples, the bioenergetics assay can measure respiratory rate, reserve respiratory capacity, or ATP linked respiration of mitochondria. An increase in respiratory rate, respiratory capacity, and/or ATP linked respiration of mitochondria indicates the agent is effective for treating the subject.

Any sample from the subject can be utilized, including, but not limited to, peripheral blood samples, white blood cell samples and/or platelet samples. The sample can also be a biopsy sample, a cerebral spinal fluid sample, a sample including fibroblasts, a muscle biopsy or a sample including muscle cells, or a urine sample.

Methods are also disclosed herein for determining the effectiveness of a first dosage, or the duration of a dosage, of a therapeutic agent for treatment of a neurodegenerative disease, such as Parkinson's disease or Parkinsonism, in a subject, such as, but not limit to, those therapeutic agents listed above. The method can determine if a therapeutic agent of interest is of use for treating a neurodegenerative disease, such as Parkinson's disease or Parkinsonism in a subject, or if the therapeutic agent has been administered for a sufficient period of time, or at a sufficient dose, to treat the subject. These methods include determining the lesion frequency in the mitochondrial DNA from a biological sample from the subject administered the therapeutic agent. A decrease in the lesion frequency in the mitochondrial DNA indicates that the agent is effective for treating a subject, or has been administered for a sufficient period of time to treat the subject. An increase in the lesion frequency, or no change in the lesion frequency in the mitochondrial DNA indicates that the agent is not effective for treating a subject. The lesion frequency in the mitochondrial DNA can be compared to a control, such as the lesion frequency in mitochondrial DNA in a sample from the subject obtained prior to treatment with the therapeutic agent.

In some embodiments, methods are disclosed for determining if an agent is effective for treating a subject with a neurodegenerative disease, such as Parkinson's disease or Parkinsonism. The methods include contacting a biological sample comprising mitochondrial DNA from a subject treated with the agent with a first forward primer comprising the nucleic acid sequence set forth as SEQ ID NO: 1, and a reverse primer comprising the nucleic acid sequence set forth as SEQ ID NO: 2, wherein the first forward primer and the reverse primer amplify a large mitochondrial DNA product of 8900 nucleotides in length.

In some embodiments, the methods also include contacting the sample with a second forward primer comprising the nucleic acid sequence set forth as SEQ ID NO: 3, wherein the second forward primer and the reverse primer amplify a short mitochondrial DNA product of 298 nucleotides in length. This amplification can occur in the same container or a different container. In one embodiments, the second forward primer is added to the same container as the first forward primer and the reverse primer. The product amplified using SEQ ID NO: 3 can serve as an internal control.

The subject can be elderly, such as greater than 60, 65, 70, 75, 80, 85 or 90 years of age.

The mitochondrial DNA is amplified in a quantitative polymerase chain reaction including a fluorescent dye, wherein the fluorescent dye has the formula

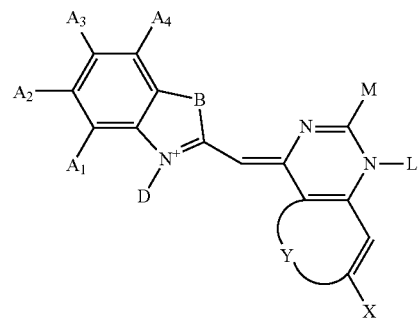

wherein all of A1, A2, A3, and A4 are H or one of A1, A2, A3, and A4 is a halogenyl and the others are H;

B is selected from the group consisting of S, O, N—R, and C—(R)$_2$ wherein R is C$_1$-C$_6$ alkyl;

D is an unsubstituted or substituted C$_1$-C$_6$ alkyl;

X is H or a methoxy group;

Y is selected from the group consisting of S, O, N—R wherein R is C$_1$-C$_6$ alkyl, and Z1-C=C—Z2 wherein Z1 and Z2 independently are H or a methoxy group;

L is CH₃ or phenyl; and

M is phenyl or a substituted or unsubstituted $C_1$-$C_{18}$ amino-alkyl to produce the large mitochondrial DNA product. Any of the alternative fluorescent dyes disclosed below can be used in these methods.

In some embodiments, the quantitative PCR is performed for 40 cycles or less, and wherein the fluorescent dye is bound to the large DNA product during amplification. The amount of the fluorescence emitted by the large DNA product is determined at multiple points during the quantitative PCR reaction to establish the linear emission range for the biological sample. The lesion frequency of mitochondrial DNA in the biological sample is determined in the linear emission range. A decrease in the lesion frequency in the linear emission range, as measured by an increase in the large mitochondrial DNA product, and a corresponding increase in fluorescence, as compared to a control lesion frequency in a control linear emission range indicates that the agent is effective for treating the subject. The control can be the lesion frequency in mitochondrial DNA in a sample from the subject prior to administration of the agent, or a standard value.

The methods can be used to determine the lowest effective therapeutic dosage of an agent for the treatment of a subject. These methods include determining the lesion frequency in the mitochondrial DNA from a biological sample from the subject administered the therapeutic agent. The lowest dose of the agent effect to decrease lesion frequency is determined. The lesion frequency in the mitochondrial DNA can be compared to a control, such as the lesion frequency in mitochondrial DNA in a sample from the subject obtained prior to treatment with the therapeutic agent.

In some embodiments, the dosage of the therapeutic agent is decreased, and a second lower dosage of the therapeutic agent is administered to the subject. In additional embodiments, these methods can be used to determine the lowest effective dosage of the therapeutic agent of use to treat the subject. In yet other embodiments, the dosage of the therapeutic is increased and administered to the subject. In other examples, and additional dosage of the therapeutic agent is administered to the subject. Thus, in additional embodiments, the method can include administering to the subject a second dosage of the therapeutic agent, wherein the second dosage is the same, greater, or less than the first dosage of the therapeutic agent.

The methods can be repeated 1, 2, 3, 4, 5, 6, 7, 8, 9, 10 or more times to determine the lowest dosage of a therapeutic agent that is effective for treating the subject, and/or the shortest duration of administration that is effective for treating the subject. The methods can also be used over the course of a therapeutic regimen to monitor the efficacy of a therapeutic agent for the treatment of the subject.

Any of the methods disclosed herein can include performing a bioenergetics assay on a white blood cell or a platelet sample from the subject. The bioenergetics assay can measure respiratory rate, reserve respiratory capacity, or ATP linked respiration of mitochondria. An increase in respiratory rate, respiratory capacity, and/or ATP linked respiration of mitochondria indicates the agent is effective for treating the subject.

In certain aspects, these assays are performed at a diagnostic laboratory, and the information is then provided to the subject or a physician or other healthcare provider.

Polymerase Chain Reaction (PCR)

The methods disclosed herein include contacting a biological sample comprising mitochondrial DNA with a first forward primer comprising the nucleic acid sequence set forth as SEQ ID NO: 1 (5'-TCT AAG CCT CCT TAT TCG AGC CGA-3', 599-), and a reverse primer comprising the nucleic acid sequence set forth as SEQ ID NO: 2 (5'-TTT CAT CAT GCG GAG ATG TTG GAT GG-3', 14841), wherein the first forward primer and the reverse primer amplify a large mitochondrial DNA product of about 8900 nucleotides in length. Several embodiments of the methods disclosed herein use quantitative polymerase chain reaction (qPCR). The amount of large mitochondrial DNA amplified in a sample (for example, 8900 nucleotides) indicates the mitochondrial lesion frequency. When a lesion is present in mitochondrial DNA, the large mitochondrial DNA product will not be produced.

The disclosed method include quantitating the amount of the fluorescence emitted by the large DNA product at multiple points during the quantitative PCR reaction to establish the linear emission range for the biological sample. The lesion frequency of mitochondrial DNA in the biological sample is determined in the linear emission range from this amplification reaction. An increase in the lesion frequency in the linear emission range as compared to a control lesion frequency in a control linear emission range indicates that the subject has the neurodegenerative disease, such as Parkinson's disease or Parkinsonism.

In some embodiments the methods include amplifying the mitochondrial DNA with a second forward primer comprising the nucleic acid sequence set forth as SEQ ID NO: 3 5'-CCC CAC AAA CCC CAT TAC TAA ACC CA-3', 14620, and the reverse primer comprising the nucleic acid sequence set forth as SEQ ID NO: 2 (5'-TTT CAT CAT GCG GAG ATG TTG GAT GG-3', 14841), wherein the second forward primer and the reverse primer amplify a small mitochondrial DNA product of about 248 nucleotides in length. The amount of small mitochondrial DNA product (for example, 248 nucleotides) is used to confirm the reaction is proceeding appropriately. Thus, the amount of small mitochondrial DNA product is the same, or does not differ significantly from the amount of small mitochondrial DNA product in a control sample, such as in a sample from a subject not known to have Parkinson's disease or a standard value. Thus, the amount of the small mitochondrial DNA product serves as an internal control to monitor reaction efficiency.

In several embodiments, multiplex qPCR assays are used to amplify and detect the large mitochondrial DNA and the small mitochondrial DNA nucleic acid molecules as described above. In the multiplex qPCR assays, the large and small mitochondrial DNA molecules are amplified and detected in a single reaction.

PCR reaction conditions typically include either two or three step cycles. Two step cycles have a denaturation step followed by a hybridization/elongation step. Three step cycles include a denaturation step followed by a hybridization step during which the primer hybridizes to the strands of DNA, followed by a separate elongation step. The polymerase reactions are incubated under conditions in which the primers hybridize to the target sequences and are extended by a polymerase. The amplification reaction cycle conditions are selected so that the primers hybridize specifically to the target sequence and are extended. The presently disclosed methods amplify mitochondrial DNA.

In a typical PCR cycle, a sample including a DNA polynucleotide and a PCR reaction cocktail is denatured by treatment in a thermal cycler at about 90-98° C. for 10-90 seconds. The denatured polynucleotide is then hybridized to oligonucleotide primers by treatment in a thermal cycler at a temperature of about 30-66° C. for 0.5-2 minutes, or for up to ten minutes, such as about 1, 2, 3, 4, 5, 6, 7, 8, 9, or 10 minutes. Chain extension then occurs by the action of a DNA polymerase on the polynucleotide annealed to the oligonucleotide primer. This reaction occurs at a temperature of about 68-72° C. for 30 seconds to 5 minutes. The polymerase can be any polymerase of interest, such as KAPA long range DNA polymerase (KAPA Biosystems) or Taq polymerase. In one specific example, the polymerase is KAPA long range DNA polymerase or another long range polymerase.

In one specific non-limiting example, the reaction is reaction cocktail is denatured by treatment in a thermal cycler at about 95° C. for about 15 seconds, hybridized to oligonucleotide primers at 66° C. for about 10 minutes, and then extended at about 72° C. for about 1 minute.

Any desired number of PCR cycles may be carried out depending on variables including but not limited to the amount of the initial DNA polynucleotide, the length of the desired product and primer stringency. The above temperature ranges and the other numbers are exemplary and not intended to be limiting. These ranges are dependent on other factors such as the type of enzyme, the type of container or plate, the type of biological sample, the size of samples, etc. One of ordinary skill in the art will recognize that the temperatures, time durations and cycle number can readily be modified as necessary.

In some embodiments, the reaction is carried out for 40 cycles or less, such as 39, 38, 37, 36, 35, 34, 33, 32, 31 or 30 cycles. Thus, in some embodiments, the steps can be repeated between 10 to 40 times, such as 15 to 40 times, such as 20 to 40 times. The steps can be repeated 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40 times. One of skill in the art appreciates that detecting the of the large mitochondrial DNA production and optionally the small mitochondrial DNA product, using PCR (such as qPCR) assays can include detecting the presence or absence (or amount) of the large mitochondrial DNA product and the small mitochondrial DNA product after a particular amplification cycle of the PCR (e.g., qPCR) assay. For example, after 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 and/or 40 amplification cycles of the PCR (e.g., qPCR) assay, or at least that may cycles, or no more than that many cycles.

Appropriate biological samples include all clinical samples useful for detection of disease in subjects. Exemplary biological samples include, without limitation, cells (such as white blood cell or platelet samples, cell lysates, blood smears, cytocentrifuge preparations, cytology smears, bodily fluids (e.g., blood, plasma, serum, saliva, sputum, urine, bronchoalveolar lavage, semen, CSF, etc.), tissue biopsies or autopsies, fine-needle aspirates, buffy coat, and/or tissue sections. In one embodiment, the biological sample is a platelet sample. In another embodiment, the biological sample is a white blood cell sample. Standard techniques for acquisition of such samples are available (see, e.g. Schluger et al., *J. Exp. Med.* 176:1327-33, 1992; Bigby et al., *Am. Rev. Respir. Dis.* 133:515-18, 1986; Kovacs et al., *NEJM* 318: 589-93, 1988; and Ognibene et al., *Am. Rev. Respir. Dis.* 129:929-32, 1984). The sample can be used directly or can be processed, such as by adding solvents, preservatives, buffers, or other compounds or substances. In some embodiments, nucleic acids are isolated from the sample. DNA or RNA can be extracted using standard methods. For instance, rapid DNA preparation can be performed using a commercially available kit (e.g., the Qiagen Tissue Kit, Qiagen, Inc., Valencia, Calif.). The DNA preparation technique can be chosen to yield a nucleotide preparation that is accessible to and amenable to nucleic acid amplification.

In some embodiments, a biological sample is obtained from a subject having, suspected of having, or at risk of having, the neurodegenerative disease, such as Parkinson's disease or Parkinsonism. In some embodiments, a decrease in the amount of the large DNA product, as compared to a control, indicates that the subject has the neurodegenerative disease, such as Parkinson's disease or Parkinsonism. In other embodiments, the subject has the neurodegenerative disease, such as Parkinson's disease or Parkinsonism, and has been administered a therapeutic agent for treatment. An increase in the amount of the large DNA product, as compared to a control, such as a sample from the same subject or other subject with Parkinson's disease not administered the therapeutic agent, indicates that the agent is effective for treatment. In a specific non-limiting example the neurodegenerative disease is Parkinson's Disease.

Any type of thermal cycler apparatus can be used for the amplification of nucleic acids as described above. Examples of suitable apparatuses include PTC-100® Peltier Thermal Cycler (MJ Research, Inc.; San Francisco, Calif.), a ROBO-CYCLER® 40 Temperature Cycler (Agilent/Stratagene; Santa Clara, Calif.), or GENEAMP® PCR System 9700 (Applied Biosystems; Foster City, Calif.). For real-time PCR, any type of real-time thermocycler apparatus can be used. For example, ICYCLER IQ™ or CFX96™ real-time detection systems (Bio-Rad, Hercules, Calif.), LIGHTCYCLER@ systems (Roche, Mannheim, Germany), a 7700 Sequence Detector (Perkin Elmer/Applied Biosystems; Foster City, Calif.), ABI™ systems such as the 7000, 7300, 7500, 7700, or 7900 systems (Applied Biosystems; Foster City, Calif.), or an MX4000™, MX3000™ or MX3005™ qPCR system (Agilent/Stratagene; Santa Clara, Calif.), DNA ENGINE OPTICON® Continuous Fluorescence Detection System (Bio-Rad, Hercules, Calif.), ROTOR-GENE® Q real-time cycler (Qiagen, Valencia, Calif.), or SMARTCYCLER® system (Cepheid, Sunnyvale, Calif.) can be used to amplify and detect nucleic acid sequences in real-time. In some embodiments, real-time PCR is performed. The reaction is initiated by adding a sample including nucleic acids and assay reagents (such as a PCR master mix) and running the reactions in a real-time thermocycler apparatus. In additional embodiments, visualization of the PCR reaction, such as in real time, is performed using the LUMINEX® MAGPIX® PCR system.

qPCR monitors the fluorescence emitted during the reaction as an indicator of amplicon production during each PCR cycle, as opposed to endpoint detection. The real-time progress of the reaction can be viewed in some systems. Typically, real-time PCR uses the detection of a fluorescent reporter. Typically, the fluorescent reporter's signal increases in direct proportion to the amount of PCR product in a reaction. By recording the amount of fluorescence emission at each cycle, it is possible to monitor the PCR reaction during exponential phase where the first significant increase in the amount of PCR product correlates to the initial amount of target template. The higher the starting copy number of the nucleic acid target, the sooner a significant increase in fluorescence is observed. Thus, the procedure follows the general pattern of polymerase chain reaction, but the nucleic acid molecule is quantified after each round of amplification. In several embodiments the amplified nucleic acid molecule is quantified by the use of fluorescent dye that intercalates with double-strand DNA.

An number of intercalating dyes are known, including but not limited to SYBR green, SYBR blue, DAPI, propidium iodine, Hoeste, SYBR gold, ethidium bromide, acridines, proflavine, acridine orange, acriflavine, fluorcoumanin, ellipticine, daunomycin, chloroquine, distamycin D, chromomycin, homidium, mithramycin, ruthenium polypyridyls, anthramycin. For example, a DNA binding dye such as SYBR green binds double stranded (ds) DNA and an increase in fluorescence intensity can be measured. For example, the fluorescent dsDNA dye can be added to the buffer used for a PCR reaction. The PCR assay can be performed in a thermal cycler, and after each cycle, the levels of fluorescence are measured with a detector, such as a camera. The dye fluoresces much more strongly when bound to dsDNA (e.g., amplified PCR product). Because the amount of the dye intercalated into the double-stranded DNA molecules is typically proportional to the amount of the amplified DNA products, the amount of amplified nucleic acid can be quantified by detecting the fluorescence of the intercalated dye using detection instruments known in the art. When referenced to a standard dilution, the dsDNA concentration in the PCR can be determined.

Fluorescent Dyes of Use

In specific embodiments, the disclosed methods utilize a fluorescent dye that binds double stranded DNA (dsDNA) that includes a benzothiazolium moiety and a pyrimidinium moiety connected by a mono-methine bridge, characterized in that (i) the 2-position of the pyrimidine carries a substituent which starts with a C-atom and (ii) the 5- and 6-positions of the pyrimidine ring are an integral part of a further aromatic ring structure. Such dyes are disclosed, for example, in U.S. Pat. No. 8,058,431, which is incorporated herein by reference in its entirety. This U.S. Patent discloses dyes having the formula: In a specific non-limiting example, the dye is used at 0.25 to 2 μL per reaction, such as about 0.5 μL per reaction.

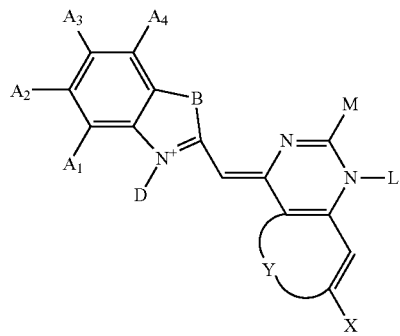

characterized in that either all of $A_1$, $A_2$, $A_3$ and $A_4$ are H or one of $A_1$, $A_2$, $A_3$ and $A_4$ is a substituent which is preferably a Halogenyl (e.g., a halogen), and the others are H B is selected from a group consisting of S, O, N—R, and C—(R)$_2$ wherein R is $C_1$-$C_6$-alkyl D is either an unsubstituted or a substituted $C_1$-$C_6$ alkyl, X is either H or a methoxy-group, '

Y is selected from a group consisting of S, O, N—R wherein R is $C_1$-$C_6$-alkyl, and Z1-C=C—Z2, wherein Z1 and Z2 independently from each other are either H or a methoxy-group L is either $CH_3$ or phenyl M is either phenyl or a substituted or unsubstituted $C_1$-$C_{18}$ amino-alkyl.

One important feature of such a fluorescent dye comprising a benzothiazolium moiety and a pyrimidinium moiety connected by a mono-methine bridge is that the 2-position of the pyrimidine carries a substituent which starts with a C-atom. As a consequence, such a fluorescent compounds has an increased thermal and chemical stability as compared to other fluorescent dyes known in the art.

Another important feature is that the 5- and 6-positions of the pyrimidine ring are an integral part of a further aromatic ring structure. Together these two ring structures form a Quinazoline or in some embodiment other heterocyclic structures. As a consequence, the excitation and emission spectra of the fluorescent compound are different from those disclosed in PCT Publication No. WO 04/38038 and US 2005/233335, but similar to that of SYBRGreen. Thus, the compounds can be detected by the same detection channels which are explicitly configured for the detection of SYBR-Green. Furthermore, within a given frame, said emission spectra may be modulated by choosing the one or other alternative from the X and Y substituents of said compound.

In some embodiments, only one representative of $A_1$, $A_2$, $A_3$ and $A_4$ is a substitution. In some non-limiting examples, such a substitution is a Halogenyl, which is most preferably a fluoro atom. Also in some non-limiting examples, B is a Sulphur atom.

In cases, wherein the fluorescent compound is used as a dye which is not conjugated to a second chemical moiety, D is a methyl group or another $C_2$-$C_6$ alkyl group. However, in cases, where the fluorescent compound is connected to a second chemical entity, D is D is either —(CH$_2$)n-COOH or —(CH$_2$)n-CO—O Succinimid, characterized in that n is a natural number between 1 and 6. In some examples, for these cases n is either 3 or 4. The fluorescent compound can then be bound via the respective groups to any kind of other molecule, and in particular to biomolecules, such as the 5' end of an oligonucleotide.

In one embodiment, L is a phenyl and M is a substituted or unsubstituted $C_1$-$C_{18}$ amino-alkyl. Alternatively, M is a phenyl and L is a methyl group. Still alternatively, L is a methyl group and M is a substituted or unsubstituted $C_1$-$C_{18}$ amino-alkyl. Embodiments wherein L and M are phenyl are less preferred, because these molecules tend to have less DNA intercalating properties. In particular, M may be —(CH$_2$)n-N$^+$—(CH$_3$)$_3$, wherein n is a natural number between 1 and 18.

The additional aromatic ring structure connected to the pyrimidine via its 5- and 6-position (as defined within the pyrimidine itself) in one embodiment is a phenylen ring, such that a Quinazoline is formed. This phenylen ring can be substituted with one or two methoxy groups at position 6 and/or 7 of the Quinazoline ring system.

In another embodiment, the aromatic ring structure is a penta-heterocycle having a sulphur atom forming a thieno [3,2-d]pyrimidine.

Furthermore, when such compounds according to the invention are present in solid status, the counter-ion can be a halogen such as iodine or chloride.

Compounds are of use that have the following structures:
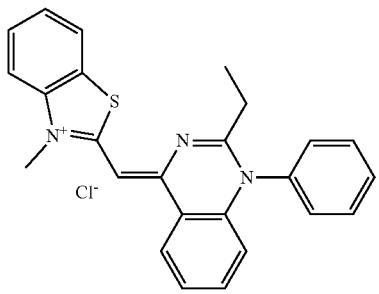
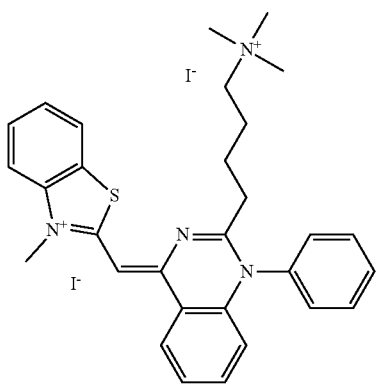
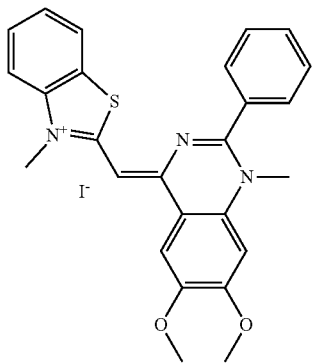
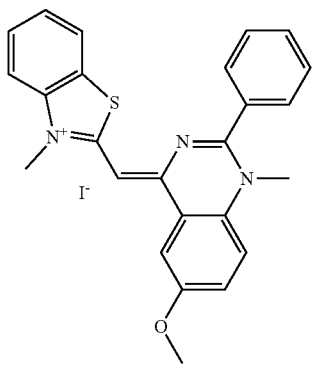
R03
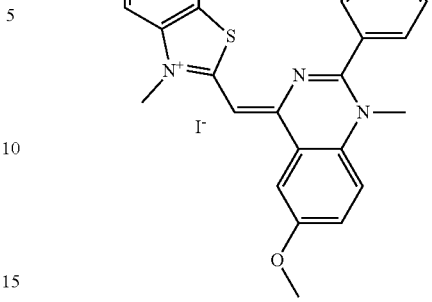
R04
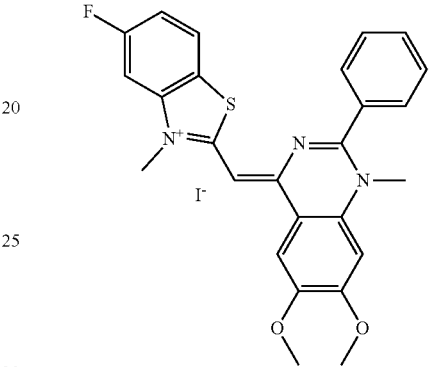
R11
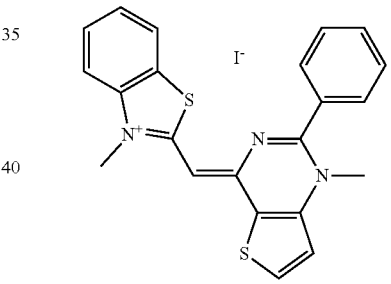
R12
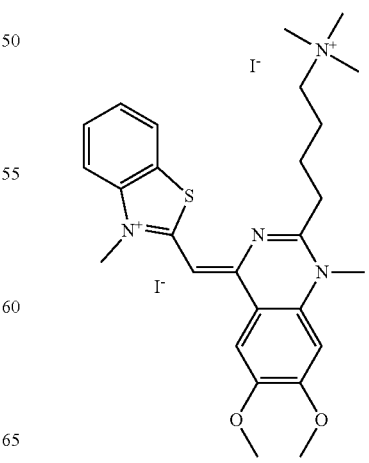

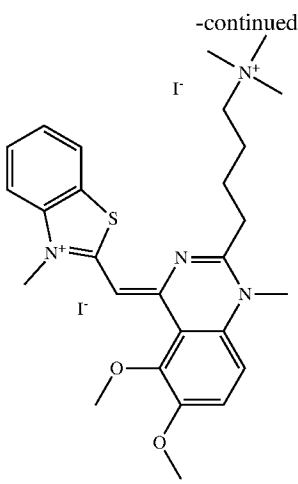

Methods for synthesizing these compounds are disclosed in U.S. Pat. No. 8,058,431, which is incorporated herein by reference.

In specific embodiments, the fluorescent dye has the formula

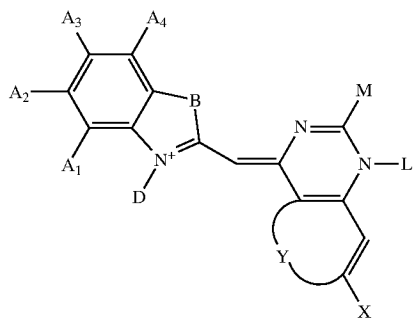

wherein all of $A_1$, $A_2$, $A_3$, and $A_4$ are H or one of $A_1$, $A_2$, $A_3$, and $A_4$ is a halogenyl and the others are H;
B is selected from the group consisting of S, O, N—R, and C—(R)$_2$ wherein R is $C_1$-$C_6$ alkyl;
D is an unsubstituted or substituted $C_1$-$C_6$ alkyl;
X is H or a methoxy group;
Y is selected from the group consisting of S, O, N—R wherein R is $C_1$-$C_6$ alkyl, and Z1-C=C—Z2 wherein Z1 and Z2 independently are H or a methoxy group;
L is $CH_3$ or phenyl; and
M is phenyl or a substituted or unsubstituted $C_1$-$C_{18}$ amino-alkyl In specific non-limiting examples, wherein D is —(CH$_2$)n-COOH or —(CH$_2$)n-CO—O succinimide, wherein n is a natural number between 1 and 6. In other non-limiting examples, M is —(CH$_2$)$_n$—N$^+$—(CH$_3$)$_3$, wherein n is a natural number between 1 and 18. In further non-limiting examples, wherein Y is Z1-C=C—Z2 wherein Z1 and Z2 independently are H or a methoxy group. In other non-limiting examples, the fluorescent dye is 2-(4-Dimethylamino-butyl)-6,7-dimethoxy-1-methyl-1H-quinazoline-4-one (RESOLIGHT).

The dye can be used at saturating concentrations to achieve highly homogeneous staining of amplicons and measurement of DNA formation in real-time PCR and DNA double-strand dissociation in melting analysis. Without being bound by theory, the dye shows an enhanced sharpness of fluorescent signals with an excitation and emission wavelength similar to fluorescein. The dye can be detected with most of the available real-time PCR instruments, without inhibiting the PCR enzyme.

The dye can be used in order to detect double stranded nucleic acids. Asymmetric carbocyanine dyes are known to intercalate into double stranded nucleic acids such as double stranded DNA and/or bind into the minor groove of a DNA double helix. Thus, the dye can be used for detection of double stranded nucleic acids, such as in PCR, such as qPCR. The dye is part of a PCR reaction mixture and it is present at the beginning of the amplification reaction.

A mixture of use includes the dye, a thermostable DNA Polymerase a mix of deoxynucleoside triphosphates which is usually dA, dG, dC and dT, and a buffer. The mixture also includes and at least one pair of amplification primers, such as a primer including the nucleic acid sequence set forth as SEQ ID NO: 1 and a primer including the nucleic acid sequence set forth as SEQ ID NO: 2. Optionally, a primer including the nucleic acid sequence set forth as SEQ ID NO: 3 is also included. The concentrations of use can be determined by those of skill in the art, and can be optimized for specific adaptations. The concentration of the dye can be from 0.1 to 10.0 μg/ml, and preferably 0.6 μg/ml.

Determining Lesion Frequency

The lesion frequency of mitochondrial DNA can be determined in the biological sample. The linear emission range of the large DNA product is determined using a computer to produce a graphical depiction of the mitochondrial DNA lesion frequency. This graphical depiction presents the amount of amplification product over time, as measured by fluorescence from the dye intercalated in the double stranded reaction product. The amount of amplified DNA product is a direct measurement of the lesion frequency. The larger the number of lesions, the less full-length reaction product is produced, and thus lower fluorescence is observed.

The following calculation can be used:

$$Y = F_{Min} + \left( \frac{F_{Max} - F_{Min}}{1 + 10^{(C_{50}-X)*Slope}} \right)$$

wherein Y is observed fluorescence at a selected PCR cycle, $F_{Min}$ is a lowest fluorescence observed during the quantitative PCR reaction, $F_{Max}$ is a maximum fluorescence observed during the quantitative PCR reaction, $C_{50}$ is the number of cycles that produces 50% of $F_{Max}$, X is the cycle number that produces 50% of $F_{Max}$, and Slope is the slope of a curve in the linear emission range of the PCR reaction.

Once the optimal number of cycles is identified (essentially an EC$_{50}$), the resulting fluorescence values (Y) are calculated for all samples, for example, healthy and/or Parkinson's subjects. The fluorescence values (in triplicate) are averaged and it is these values that are the basis for the relative amplification, which is the comparison between the healthy subjects and the Parkinson's subjects. The lesion frequency is then calculated using the following equation which is based on a Poisson expression:

−*ln*(Y=Parkinson's sample/Y=Healthy subject)

This value is further normalized for mitochondrial copy number using an internal control, such as, but not limited to the product amplified by a primer including the nucleic acid sequence set forth as SEQ ID NO: 1 and a primer including the nucleic acid sequence set forth as SEQ ID NO: 3. To normalize, each sample's small mitochondrial product value is divided by the average of all small mitochondrial products, in order to obtain a correction factor for each sample. Then, each sample's large mitochondrial value by is divided by the correction factor. Thus, the normalized mtDNA lesion frequency is calculated.

In some embodiments, lesion frequency is also determined for a control sample. The control can be the lesion frequency in a sample from a subject that does not have the neurodegenerative disease, such as Parkinson's disease and Parkinsonism. Thus, an increase in lesion frequency as compared to the control, indicates that the subject has Parkinson's disease. In another embodiment, the control can be a standard value. Thus, the control can be the average lesion frequency in healthy subjects (that do not have Parkinson's disease).

In other embodiments, the subject is a subject with Parkinson's disease that has been administered a therapeutic agent. The control is a sample from the subject, prior to administration of the therapeutic agent. A decrease in the lesion frequency as compared to the control indicates that the therapeutic agent is effective for treating the subject. In a further embodiment, the control can be a standard value. Thus, the control can be the average lesion frequency in subjects with Parkinson's disease that are not receiving treatment.

The calculation can be performed by a multipurpose computer, using a spreadsheet program such as EXCEL®, or a computer specific to a designated PCR machine.

Additional Assays for Mitochondrial Function

The methods can also include performing a bioenergetics assay on a sample from the subject, such as a white blood cell or platelet sample from the subject. The bioenergetics assay can measure, for example, respiratory rate, reserve respiratory capacity, or ATP linked respiration of mitochondria in the platelet sample or white blood cell sample.

The synthesis of ATP via oxidative phosphorylation is the most common function of mitochondria, and is a process is typically determined indirectly through measurement of mitochondrial oxygen ($O_2$) consumption, or respiration. Altered respiratory kinetics in response to specific substrates are often interpreted as reflecting changes in oxidative phosphorylation and the regulation of cellular energy homeostasis. According to Perry et al. (Diabetes 62: 1041-1053, 2013, incorporated herein by reference), the rate of mitochondrial respirometric $O_2$ flux can be a measured by several methods in the art. These methods include $O_2$-dependent quenching of porphyrin-based phosphors and amperometric $O_2$ sensors. Phosphorescent probes have also been used for in vitro/in situ respiratory measurements (e.g., the Seahorse Bioscience XF Extracellular Flux Analyzer or Luxcel MitoXpress). An amperometric approach is also of use.

In some examples, a Clark electrode can be utilized. A Clark electrode contains a gold or platinum cathode and an Ag/AgCl anode separated by a KCl solution. A voltage is applied to the two half-cells, which are separated from the experimental assay media by a membrane of $O_2$-permeant material (e.g., polyvinylidene difluoride). 02 diffuses from the assay media through the membrane and is reduced by electrons at the cathode, yielding hydrogen peroxide ($H_2O_2$). The $H_2O_2$ then oxidizes the Ag of the Ag/AgCl anode, which generates an electrical current proportional to the partial pressure, and in turn concentration, of $O_2$ in the experimental solution. Changes in [$O_2$] in the assay media (typically 1-2 mL) therefore correspond to the inverse of the respiratory rate of a biological sample (e.g., mitochondria) and allow for quantification of $O_2$ consumption (Perry et al., supra).

The XF Extracellular Flux Analyzer (Seahorse Bioscience) can be used for measurement in intact adherent cells in culture. This system uses a 24- or 96-well cell culture microplate format that is mated from above with a sensor cartridge containing an equivalent number of individual probes, each containing fluorophores sensitive to $O_2$ or $H^+$ embedded within the polymer that comprises the probe. A piston-like sensor cartridge is introduced periodically into the wells of the microplate, forming transient microchambers just above (~200 microns) the cell monolayer. Fiber optic bundles inserted simultaneously by the machine into the probes of the sensor cartridge provide the excitation and collect the emission light for each fluorophore. The change in $O_2$ and $H^+$ concentration in the media (7-10 μL) is measured over several minutes, reflecting the rate of cellular $O_2$ consumption and $H^+$ production. Raising the sensor cartridge then allows the media above the cells to mix/reequilibrate. The XF Extracellular Flux Analyzer can also measure extracellular acidification rates and carbon dioxide evolution rates as indices of glycolysis and tricarboxylic acid cycle (TCA) kinetics (Perry et al., supra).

Mitochondria regulate cellular redox homeostasis through the establishment of the redox circuitry (e.g., via the NADPH/NADP couple) and emission of reactive oxidants. Reactive $O_2$ species (ROS) are molecules that are chemically reactive due to the incomplete reduction of $O_2$ within the molecule. These include free radicals possessing an unpaired electron such as the superoxide anion ($O_2\cdot^-$), hydroxyl radical (HO·, peroxyl and nitroxyl radicals, as well as nonradical oxidants such as $H_2O_2$. Thus, the disclosed methods can include measurement of ROS.

Electron spin resonance/electron paramagnetic resonance can be used to measure free radicals, an approach that can be used in vivo under physiological conditions. A variation on the technique, known as spin trapping, is also frequently used; it incorporates a detecting molecule that reacts with, but is considerably more stable than, the initial free radical. The resulting free radical product often has spectral properties that allow the original radical to be identified indirectly. Although clinical applications continue to develop. Several fluorescent-, chemiluminescent-, and electrochemical/nanoparticle-based approaches are known in the art for the detection of oxidants. These include 2',7'-dichlorodihydrofluorescein, triphenylphosphonium hydroethidine-based probe MITOSOX™ Red, and AMPLEX® Red (N-acetyl-3,7-dihydroxyphenoxazine, detects H2O2), see Perry et al, supra.

Mitochondrial oxidant production can also be measured. These methods are known in the art, and can utilize substrates in combination with inhibitors to specific sites within the respiratory complexes have been used to identify the sites and topology of $O_2\cdot^-$ production.

Membrane potential also can be measured. In some examples, cationic fluorescent probes can be used to qualitative changes in mitochondrial membrane potential in cultured cells using confocal microscopy and/or flow cytometry.

ATP production rate can also be measured. ATP production provides an index of oxidative phosphorylation activity in isolated mitochondria. The ATP produced is detected. In some examples, ATP production is detected through the reaction of luciferin with ATP, to ultimately generate oxyluciferin, AMP, and light via firefly luciferase, which is detected in a luminometer.

The sensitivity of the permeability transition pore to calcium loading has been used as an index of mitochondrial viability and can be detected. In some embodiments, this is evaluated by determining the calcium retention capacity of mitochondria to CALCIUM GREEN™-5N (Molecular Probes), a relatively low-affinity impermeable calcium indicator that exhibits increased fluorescence emission intensity upon binding calcium. Pulses of calcium are added at defined intervals, each eliciting a spike in signal that dissipates due to the uptake of calcium into the mitochondrial matrix. Calcium concentration can be monitored continuously with each addition until opening of the Permeability Transition Pore collapses the membrane potential and releases the accumulated calcium from the matrix, causing a sudden and sustained increase in signal. The amount of calcium retained prior to opening of the Permeability Transition Pore is considered an index of mitochondrial viability. Additional methods are disclosed in Perry et al. supra, see //diabetes.diabetesjournals org/content/62/4/1041.full)

Kits

The oligonucleotide probes and/or primers and compositions, including such probes and/or primers disclosed herein, and a fluorescent dye, can be supplied in the form of a kit for use in identification of a neurodegenerative disease, such as Parkinson's disease or Parkinsonism, or to determine the effect of therapeutic agents. In such a kit, one or more of the oligonucleotide probes and/or primers is provided in one or more containers. An oligonucleotide primer can be provided suspended in an aqueous solution, or as a freeze-dried or lyophilized powder. The container(s) in which the oligonucleotide(s) are supplied can be any conventional container that is capable of holding the supplied form; e.g., microfuge tubes, ampoules, or bottles. In some applications, pairs of primers can be provided in pre-measured single use amounts in individual, typically disposable, tubes or equivalent containers. With such an arrangement, the sample to be tested can be added to the individual tubes and amplification carried out directly, followed by sequence analysis, if desired or warranted but not necessary.

In some embodiments, the kit includes a container including a first oligonucleotide primer pair including a forward oligonucleotide primer and a reverse oligonucleotide primer, wherein the forward oligonucleotide primer the nucleic acid sequence set forth as SEQ ID NO: 1 and wherein the reverse oligonucleotide primer comprises the nucleic acid sequence set forth as. The container can further include a third nucleic acid primer including the nucleic acid sequence set forth as SEQ ID NO: 3. Thus, in some embodiments, three primers are formulated for use in a multiplex qPCR assay.

In some embodiments, kits can also include the reagents necessary to carry out PCR amplification reactions (including qPCR reactions), including DNA sample preparation reagents, appropriate buffers (e.g., polymerase buffer), salts (e.g., magnesium chloride), and deoxyribonucleotides (dNTPs). One or more control sequences for use in the PCR reactions can also be supplied in the kit. The kit can also include a dye for visualizing amplified DNA (see above).

In one embodiment, kits are supplied with instructions. In one specific, non-limiting example, the instructions are written instructions. In another such example, the instructions are provided in electronic format. The instructions may, for example, instruct the user how to use the primers and probes to amplify and detect the nucleic acid sequences using the methods described herein. The instructions may also include information on how to calculate lesion frequency.

The disclosure is illustrated by the following non-limiting Examples.

EXAMPLES

Example 1

Protocol for mitochondrial DNA damage assay
Materials/Equipment
1. Quanti-iT PicoGreen dsDNA reagent—Molecular Probes—P114952.
2. Lambda/HindIII DNA
3. 1×TE buffer: 10 mM Tris-HCL pH 8.0, 1 mM EDTA
4. Fluorescent plate reader with excitation filter at 480 nm and an emission filter at 520 nm (485 nm and 528 nm also work well) SpectraMax—Gemini EM
5. 96-well plate MicroAmp Optical 96—Well Reaction Plate—Applied Biosystems (Life)—4306737
6. PCR strips MicroAmp 12—cap Strip—Applied Biosystems (Life)—N8010534
7. Long Range DNA Polymerase Kit—Kapa Biosystems—KK3503
8. LightCycler 480 ResoLight Dye—Roche—04 909 640 001
9. PCR hood with germicidal lamp for sterilization
10. Primers, species and target genome specific.
Primers for human experiments
Small Mito—14620: 5'-CCC CAC AAA CCC CAT TAC TAA ACC CA-3' (SEQ ID NO: 3)
Large Mito—5999: 5'-TCT AAG CCT CCT TAT TCG AGC CGA-3' (SEQ ID NO: 1)
Large+Small—14841: 5'-TTT CAT CAT GCG GAG ATG TTG GAT GG-3' (SEQ ID NO: 2)
11. 0.1 mg/mL bovine serum albumin in nuclease free $H_2O$—Sigma—A6003
12. 10 mM dNTPs Mix—KAPA Long Range DNA Polymerase Kit—Kapa Biosystems—KK3503
12. Nuclease-Free $H_2O$—Qiagen—129114
13. Dedicated pipettes and sterile aerosol pipet tips for QPCR set up
14. Different set of pipettes and regular tips for post-PCR analysis
15. Distinct workstations for setting up and post-PCR analysis
16. Agilent—Stratagene M×3000 P
17. 96-well Flat Bottom Bacti Plate, Non-Sterile, 0.4 mL well—Fisher—269620
18. Spectrophotometer—Nanodrop—ND-1000
DNA quantification
1. Prepare a DNA concentration standard curve by diluting Lambda/HindIII DNA to 150 ng/μL, 100 ng/μL, 50 ng/μL, 25 ng/μL, 12.5 ng/μL and Ong/μL in TE buffer. Make dilutions into sterile Eppendorf tubes using nuclease-free water.
2. Add 5 μL of DNA and 95 μL of 1× TE buffer into triplicate wells of a 96 well plate.
3. The following 3 steps should be done in low light conditions. Prepare Pico Green working solution (100 μL of working solution needed per well) by adding 5 μL Pico Green reagent per 1 ml TE buffer.
4. Mix the plate in the machine and let the plate incubate for 10 minutes.
5. Set the excitation to 485, emission to 530, and the sensitivity to 12.
6. This process should be repeated and confirmed 3 times to ensure an accurate reading.
7. Generate standard curve.

8. Using standard curve, measure DNA sample and aim for the working concentration for the DNA sample to be between 2.0 and 3.0 ng/µl.

To overcome the time- and labor-intensive mtDNA damage assay a novel platform was 96-well platform. Previously, single tubes were used to perform the mtDNA damage assay using standard PCR machines. At best, to obtain data for 6 samples would take about a week, and more typically two to several weeks.

Development of a microplate-based assay was possible by overcoming two at least two significant barriers: (1) finding a dye that was compatible for Real-Time Thermal Cyclers that was sufficient for this assay, and (2) deriving a new mathematical equation that enables us to calculate the mtDNA lesion frequency. We optimized the PCR conditions with the dye RESOLIGHT® (Fisher) and derived the equation shown above and in FIG. 1.

The assays disclosed herein provide significant advantages:
  Higher throughput, can analyze up to 25 samples in triplicate simultaneously
  More sensitive, consistent and reliable
  Protocol and analysis quicker
  Reduced overall time from weeks to days
  Reduced overall cost
  Easily adaptable to 396-well platform
  Quantitative-based PCR assay 1. In a 96-well plate the reactions are prepared as follows:
   a. A master mix is made which consists of the following components, added in this order:
      i. 10 µl 5× LongRange Buffer
      ii. 1 µl BSA (100 ng/µl)
      iii. 1 µl dNTP (10 mM)
      iv. 2.5 µl primer (10 µM dilution→0.5 uM working conc.)
      v. 2.5 µl primer (10 uM dilution→0.5 uM working conc.)
      vi. 3.5 µl Mg (25 mM)
      vii. 0.5 uL Polymerase
      viii. 0.5 uL ResoLight
      ix. vortex
   b. Aliquot master mix 21.5 uL into each well via a multichannel pipet.
   c. Add 15 ng DNA
   d. Add $H_2O$ to 50 µl total
2. Also, add '50% control' and 'No template control' to appropriate wells.
3. After all of the PCR components are added, place cap strips to cover the wells, mix/shake the plate briefly and centrifuge for 2 minutes @ 1200 rpm. Immediately take the plate over the Stratagene machine to limit exposure to light.
4. Open MxPro Software, select "SYBRGreen RT Experiment".
5. Check the boxes to collect for Rox and SYBR fluorescence data.
6. Set Rox as the reference dye.
7. Fill out the "Plate Setup" to match the 96-well layout
8. Under the "Thermal Profile Setup" tab enter the following profile settings
   Segment 1 (1 cycle)
      95° C. for 3 minutes
   Segment 2 (40 cycles)
      95° C. for 15 seconds
      66° C. for 10 minutes Data Analysis
1. Export Data: File→Export Chart Data To Excel
2. GraphPad Prism→New File→XY table & graph
   a. X-axis is labeled 1-40 for each cycle number
   b. Fill in the corresponding Y-axis values with the exported Excel data for each sample
   c. Analyze→XY analyses→Nonlinear regression (curve fit)→OK→Dose-response—Stimulation→log(agonist) vs. response—Variable slope→Least squares (ordinary) fit Algorithm:

$$Y = \frac{F_{Min} + (F_{Max} - F_{Min})}{1 + 10^{(C_{50}-X)*Slope}}$$

Final Value$=-\ln(Y\ Sample/Y\ Control)$

|  | Control | Sample |
| --- | --- | --- |
| $F_{Min}$ | −0.005464 | −0.000667 |
| $F_{Max}$ | 11.03 | 9.614 |
| $C_{50}$ | 19.12 | 19.04 |
| Slope | 0.2501 | 0.2489 |

$Y$ Sample=−0.000667+(9.614—0.000667)/(1+10^((19.04−18.86997)*0.2489))$Y$ Sample=4.572627

$X$ Control=((Log((1/(((11.03/2)−0.005464)/11.04))−1))−19.12+0.2501)$X$ Control=18.86997

$Y$ Control=−0.005464+(11.03—0.005464)/(1+10^((19.12−18.86997)*0.2501))$Y$ Control=5.115718

Final Value=−$LN$(4.572627/5.115718)=0.11223

Example 2

Data

Figure 3:
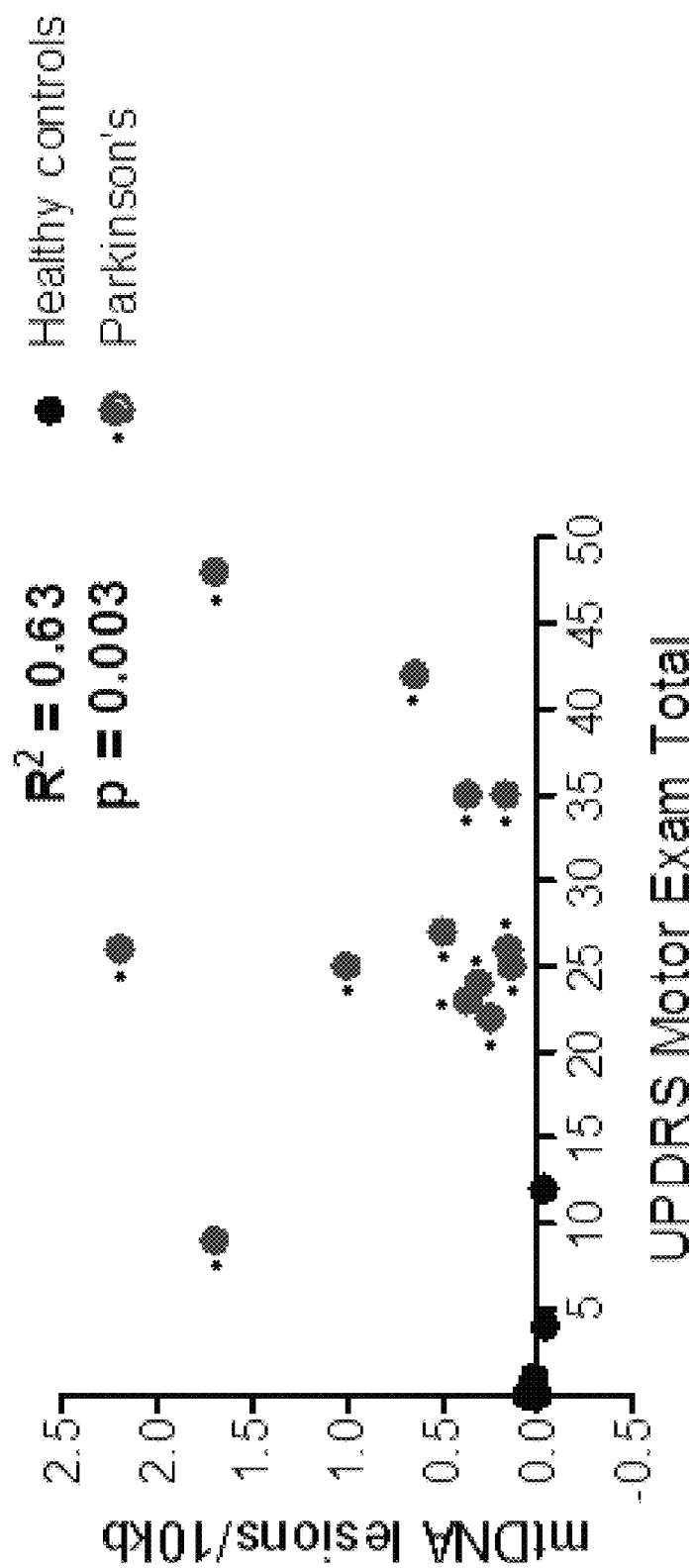
FIG. 3. The Movement Disorder Society Unified Parkinson's Disease Rating Scale (MDS-UPDRS), which is the standard rating scale to follow PD clinical disease and progression longitudinally. We found a positive correlation between UPDRS motor scores and mtDNA damage levels ($R^2$=0.63, p=0.003).
Figure 5A:
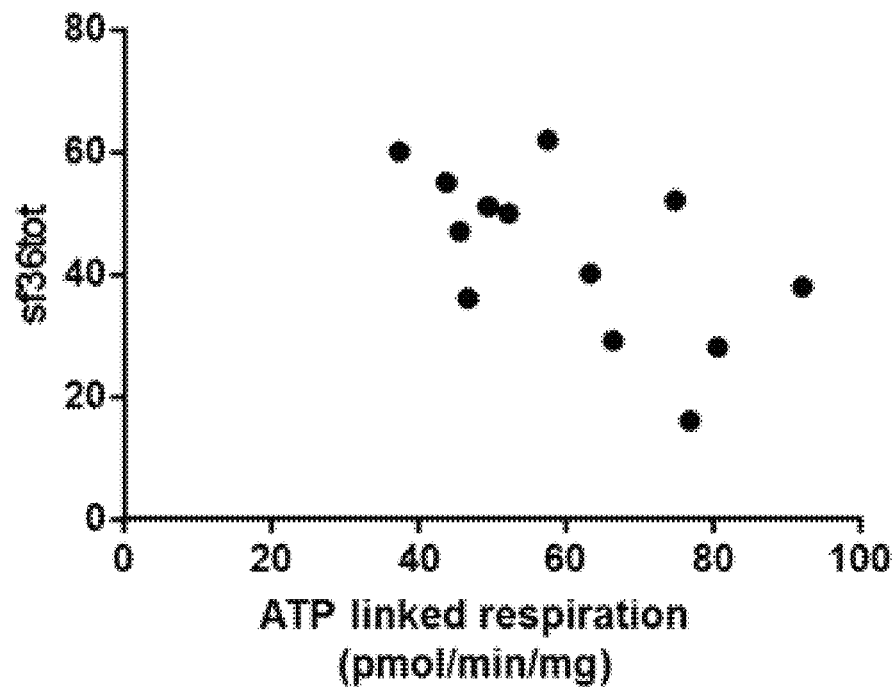
FIGS. 5A-5B show the correlation of platelet bioenergetic parameters with cognitive and motor function as assessed by the Unified Parkinson's Disease Rating Scale (UPDRS).
Figure 5B:
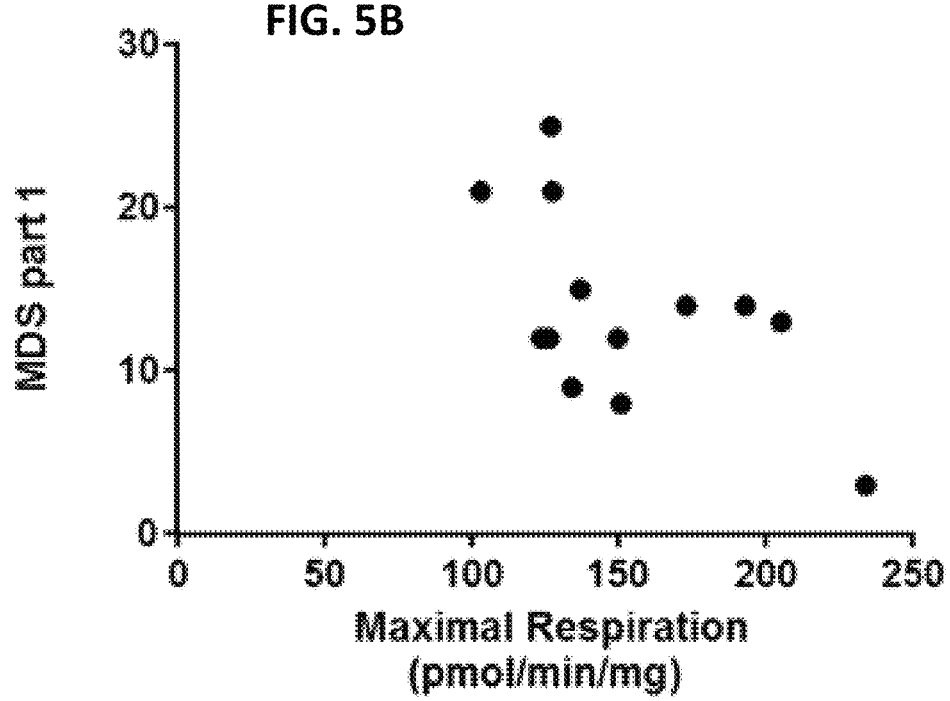

Patients with PD show increased mitochondrial DNA damage versus healthy controls:

Striking statistically significant data was obtained from a study showing that sporadic PD is associated with increased mtDNA damage in blood buffy-coat samples compared to healthy controls (see FIG. 3). Importantly, mtDNA copy number was similar across both groups. QPCR-based assay was performed blinded. Strikingly, compared to healthy controls, subjects with PD had elevated mtDNA damage (p=0.006). mtDNA copy number was similar across both groups. These results suggested that PD was associated with persisting mtDNA damage systemically.

The Movement Disorder Society Unified Parkinson's Disease Rating Scale (MDS-UPDRS) is the standard rating scale to follow PD clinical disease and progression longitudinally. A relationship was found between the severity of clinical motor features as assessed by the UPDRS and the level of mtDNA damage (see FIG. 4).

Example 3

Protocol for isolation of blood cells and measurement of bioenergetic profile in platelets and peripheral blood mononuclear cells (PBMCs)
1. Blood is drawn by standard venipuncture into cell preparation tubes (BD Vacutainer)
2. Blood is centrifuged at 150×g, 10 min, with no brake 3. Platelet rich plasma (PRP) is removed and prostaglandin $I_2$ is added (1 µg/ml) for platelet isolation. Remainder of the blood is centrifuged at 1500×g, 10 min, no brake for PBMC isolation.
1. For platelets, centrifuge at 1500×g, 10 min to pellet the platelets.
2. Resuspend the platelet pellet in Erythrocyte Lysis buffer (Qiagen 1014614; 300 µl) containing $PGI_2$ (1 ug/ml). Centrifuge the suspension (3100×g; 4 min) and remove the supernatant. This step is repeated until no traces of RBCs remain (maximum of 3 washes).
3. The final pellet should be resuspended in standard Tyrode's Buffer.
4. For PBMCs, transfer buffy coat to 15 ml conical tube and dilute 1:1 with Hank's Balanced Salt Solution
5. Centrifuge at 300× g, 5 min, with deceleration of 2 units
6. Wash the resulting pellet with Erythrocyte Lysis buffer+$PGI_2$(1:500 dilution) twice.
7. Resuspend pellet in 500 µL Seahorse Dulbecco's Modified Eagle's Medium.
8. Count PBMC and platelet cell number
9. Plate PBMCs at 500K/well density and platelets at 50 million/well density (in each well of the XF96 V7-PS Cell Culture Microplate)
10. Centrifuge plate at 50×g, 3 min, no brake.
11. Assay bioenergetic profile by Seahorse XF analysis Seahorse Analysis
1. Incubate the centrifuged plate (with monolayers of cells) for 10 minutes at 37° C. prior to measurement
2. Insert plate and read oxygen consumption and extracellular acidification. Three measurements are made of 7 minutes each before and after the following drug injections.

Drug Injections
PBMCs:
A—1 µM Oligomycin
B—300 nM FCCP (Carbonyl cyeanide-4-phenylhydrazone)
C—100 mM 2DG (2-deoxy glucose)
D—1 µM Rotenone
Platelets:
A—2.5 µM Oligo
B—0.7 µM FCCP
C—100 mM 2DG
D—15 µM Rot Example 4

Platelets from patients with PD show altered bioenergetics versus healthy controls FIG. 1 shows representative bioenergetics profiles for a PD patient and an age/race matched healthy control. As quantified in FIG. 1, patients with PD have a trend for decreased baseline and maximal respiratory rate (induced by the addition of the uncoupler FCCP). Calculation of the reserve respiratory capacity (the difference between maximal respiratory rate with FCCP and baseline rate) shows a significantly decreased capacity in the PD patients versus control. Additionally, calculation of ATP linked respiration (the difference between baseline OCR and oligomycin sensitive OCR) shows a trend towards decreased ATP linked OCR and increased proton leak in PD patients (FIGS. 2-5).

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

We claim:

1. A method of diagnosing Parkinson's disease, comprising contacting a biological sample comprising mitochondrial DNA with a first forward primer comprising the nucleic acid sequence set forth as SEQ ID NO: 1, and a reverse primer comprising the nucleic acid sequence set forth as SEQ ID NO: 2, wherein the first forward primer and the reverse primer amplify a large mitochondrial DNA product of about 8900 nucleotides in length;

amplifying the mitochondrial DNA in a quantitative polymerase chain reaction comprising a fluorescent dye, wherein the fluorescent dye has the formula wherein all of $A_1$, $A_2$, $A_3$, and $A_4$ are or one of $A_1$, $A_2$, $A_3$, and $A_4$ is a halogenyl and the others are H;

B is selected from the group consisting of S, O, N—R, and C—(R)$_2$ wherein R is $C_1$-$C_6$ alkyl;

D is an unsubstituted or substituted $C_1$-$C_6$ alkyl;

X is H or a methoxy group;

Y is selected from the group consisting of S, O, N—R wherein R is $C_1$-$C_6$ alkyl, and Z1-C=C—Z$_2$ wherein Z1 and Z2 independently are H or a methoxy group;

L is $CH_3$ or phenyl; and

M is phenyl or a substituted or unsubstituted $C_1$-$C_{18}$ amino-alkyl to produce the large mitochondrial DNA product, wherein the quantitative PCR is performed for 40 cycles or less, and wherein the fluorescent dye is bound to the large DNA product during amplification;

quantitating the amount of the fluorescence emitted by the large DNA product at multiple points during the quantitative PCR reaction to establish the linear emission range for the biological sample; and determining the lesion frequency of mitochondrial DNA in the biological sample in the linear emission range, wherein an increase in the lesion frequency in the linear emission range as compared to a control lesion frequency in a control linear emission range indicates that the subject has Parkinson's disease.

2. The method of claim 1, wherein the biological sample is a cerebral spinal fluid, saliva, or a peripheral blood sample.

3. The method of claim 1, wherein the biological sample comprises fibroblasts and/or muscle cells.

4. The method of claim 1, wherein the biological sample is a muscle biopsy.

5. The method of claim 1, wherein the fluorescent dye is:

6. The method of claim 1, wherein M is —$(CH_2)_n$—$N^+$—$(CH_3)_3$, wherein n is a natural number between 1 and 18.

7. The method of claim 1, wherein Y is Z1-C=C—Z2, wherein Z1 and Z2 independently are H or a methoxy group.

8. The method of claim 1, wherein the fluorescent dye comprises a pyrimidinium moiety provided by 2-(4-Dimethylamino-butyl)-6,7-dimethoxy-1-methyl-1H-quinazoline-4-one.

9. The method of claim 1, further comprising amplifying the mitochondrial DNA with a second forward primer comprising the nucleic acid sequence set forth as SEQ ID NO: 3 and the reverse primer comprising the nucleic acid sequence set forth as SEQ ID NO: 2, and wherein the second forward primer and the reverse primer amplify a small mitochondrial DNA product of about 248 nucleotides in length.

10. The method of claim 1, wherein determining the lesion frequency of mitochondrial DNA in the biological sample in the linear emission range comprises using a computer to produce a graphical depiction of the mitochondrial DNA lesion frequency and determine the linear emission range using the function $$Y = F_{Min} + \left( \frac{F_{Max} - F_{Min}}{1 + 10^{(C_{50}-X)*Slope}} \right)$$

wherein Y is observed fluorescence at a selected PCR cycle, $F_{Min}$ is a lowest fluorescence observed during the quantitative PCR reaction, $F_{Max}$ is a maximum fluorescence observed during the quantitative PCR reaction, $C_{50}$ is the number of cycles that produces 50% of $F_{Max}$, X is the cycle number that produces 50% of $F_{Max}$, and Slope is a slope of a curve in the linear emission range of the PCR reaction.

11. The method of claim 1, wherein D is —$(CH_2)_n$—COOH or —$(CH_2)_n$—CO—O succinimide, wherein n is a natural number between 1 and 6.

12. A method of diagnosing Parkinson's disease in a subject, comprising a) contacting a biological sample comprising mitochondrial DNA from the subject with a first forward primer comprising the nucleic acid sequence set forth as SEQ ID NO: 1, and a reverse primer comprising the nucleic acid sequence set forth as SEQ ID NO: 2, wherein the first forward primer and the reverse primer amplify a large mitochondrial DNA product of about 8900 nucleotides in length;

amplifying the mitochondrial DNA in a quantitative polymerase chain reaction comprising a fluorescent dye, wherein the fluorescent dye has the formula

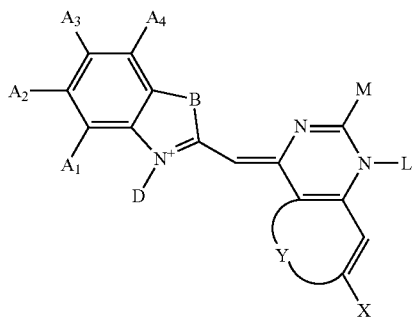

wherein all of $A_1$, $A_2$, $A_3$, and $A_4$ are H or one of $A_1$, $A_2$, $A_3$, and $A_4$ is a halogenyl and the others are H;

B is selected from the group consisting of S, O, N—R, and C—(R)$_2$ wherein R is $C_1$-$C_6$ alkyl;

D is an unsubstituted or substituted $C_1$-$C_6$ alkyl;

X is H or a methoxy group;

Y is selected from the group consisting of S, O, N—R wherein R is $C_1$-$C_6$ alkyl, and Z1-C=C—Z2 wherein Z1 and Z2 independently are H or a methoxy group;

L is $CH_3$ or phenyl; and

M is phenyl or a substituted or unsubstituted $C_1$-$C_{18}$ amino-alkyl to produce the large mitochondrial DNA product, wherein the quantitative PCR is performed for 40 cycles or less, and wherein the fluorescent dye is bound to the large DNA product during amplification;

quantitating the amount of the fluorescence emitted by the large DNA product at multiple points during the quantitative PCR reaction to establish the linear emission range for the biological sample; and determining the lesion frequency of mitochondrial DNA in the biological sample in the linear emission range, wherein an increase in the lesion frequency in the linear emission range as compared to a control lesion frequency in a control linear emission range indicates that the subject has Parkinson's disease; and b) performing a bioenergetics assay on a biological sample from the subject, thereby diagnosing Parkinson's disease in the subject.

13. The method of claim 12, wherein the bioenergetics assay measures respiratory rate, reserve respiratory capacity, or ATP linked respiration of mitochondria in the biological sample.

14. The method of claim 12, wherein the amount of mitochondrial DNA damage is increased, and wherein the method comprising administering to the subject a therapeutically effective amount of L-dopa.

15. The method of claim 12, wherein the biological sample is a cerebral spinal fluid, saliva, muscle biopsy or a peripheral blood sample.

16. The method of claim 12, wherein the biological sample comprises fibroblastsm and/or muscle cells.

17. A method of determining if an agent is effective for treating a subject with Parkinson's disease, comprising contacting a biological sample comprising mitochondrial DNA from a subject treated with the agent with a first forward primer comprising the nucleic acid sequence set forth as SEQ ID NO: 1, and a reverse primer comprising the nucleic acid sequence set forth as SEQ ID NO: 2, wherein the first forward primer and the reverse primer amplify a large mitochondrial DNA product of 8900 nucleotides in length;

amplifying the mitochondrial DNA in a quantitative polymerase chain reaction comprising a fluorescent dye, wherein the fluorescent dye has the formula

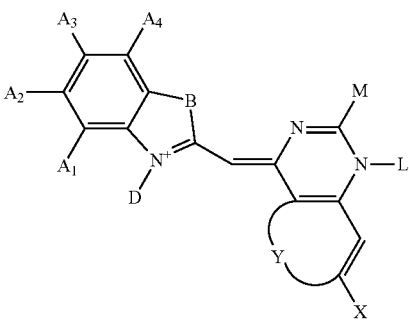

wherein all of A1, A2, A3, and A4 are H or one of A1, A2, A3, and A4 is a halogenyl and the others are H;

B is selected from the group consisting of S, O, N—R, and C—(R)$_2$ wherein R is $C_1$-$C_6$ alkyl;

D is an unsubstituted or substituted $C_1$-$C_6$ alkyl;

X is H or a methoxy group;

Y is selected from the group consisting of S, O, N—R wherein R is $C_1$-$C_6$ alkyl, and $Z_1$-C=C—Z2 wherein Z1 and Z2 independently are H or a methoxy group;

L is $CH_3$ or phenyl; and

M is phenyl or a substituted or unsubstituted $C_1$-$C_{18}$ amino-alkyl to produce the large mitochondrial DNA product, wherein the quantitative PCR is performed for 40 cycles or less, and wherein the fluorescent dye is bound to the large DNA product during amplification;

quantitating the amount of the fluorescence emitted by the large DNA product at multiple points during the quantitative PCR reaction to establish the linear emission range for the biological sample; and determining the lesion frequency of mitochondrial DNA in the biological sample in the linear emission range, wherein a decrease in the lesion frequency in the linear emission range as compared to a control lesion frequency in a control linear emission range indicates that the agent is effective for treating the subject.

18. The method of claim 17, wherein the biological sample is a cerebral spinal fluid, saliva, muscle biopsy, or a peripheral blood sample.

19. The method of claim 17, wherein the biological sample comprises fibroblasts and/or muscle cells.

20. The method of claim 17, wherein the fluorescent dye is:

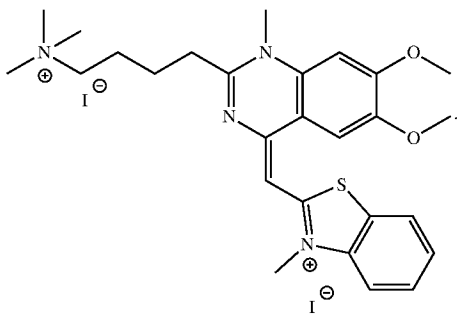

21. The method of claim 17, wherein the control is the lesion frequency in the linear emission range in a sample from the subject prior to administration of the agent.

22. The method of claim 17, wherein M is —$(CH_2)_n$—$N^+$—$(CH_3)_3$, wherein n is a natural number between 1 and 18.

23. The method of claim 17, wherein Y is Z1-C=C—Z2 wherein Z1 and Z2 independently are H or a methoxy group.

24. The method of claim 17, wherein the fluorescent dye comprises a pyrimidinium moiety provided by 2-(4-Dimethylamino-butyl)-6,7-dimethoxy-1-methyl-1H-quinazoline-4-one.

25. The method of claim 17, further comprising amplifying the mitochondrial DNA with a second forward primer comprising the nucleic acid sequence set forth as SEQ ID NO: 3 and the reverse primer comprising the nucleic acid sequence set forth as SEQ ID NO: 2, and wherein the second forward primer and the reverse primer amplify a small mitochondrial DNA product of 248 nucleotides in length.

26. The method of claim 17, wherein determining the lesion frequency of mitochondrial DNA in the biological sample in the linear emission range comprises using a computer to produce a graphical depiction of the mitochondrial DNA lesion frequency and determine the linear emission range using the function $$Y = F_{Min} + \left( \frac{F_{Max} - F_{Min}}{1 + 10^{(C_{50}-X)*Slope}} \right)$$

wherein Y is observed fluorescence at a selected PCR cycle, $F_{Min}$ is a lowest fluorescence observed during the quantitative PCR reaction, $F_{Max}$ is a maximum fluorescence observed during the quantitative PCR reaction, $C_{50}$ is the number of cycles that produces 50% of $F_{Max}$, X is the cycle number that produces 50% of $F_{Max}$, and Slope is a slope of a curve in the linear emission range of the PCR reaction.

27. The method of claim 17, wherein D is —$(CH_2)$n-COOH or —$(CH_2)$n-CO—O succinimide, wherein n is a natural number between 1 and 6.

* * * * *

SEQUENCE LISTING

```
<160> NUMBER OF SEQ ID NOS: 3

<210> SEQ ID NO 1
<211> LENGTH: 24
<212> TYPE: DNA
<213> ORGANISM: Artificial Sequence
<220> FEATURE:
<223> OTHER INFORMATION: Primer

<400> SEQUENCE: 1
tctaagcctc cttattcgag ccga                                          24

<210> SEQ ID NO 2
<211> LENGTH: 26
<212> TYPE: DNA
<213> ORGANISM: Artificial Sequence
<220> FEATURE:
<223> OTHER INFORMATION: Primer

<400> SEQUENCE: 2
tttcatcatg cggagatgtt ggatgg                                        26

<210> SEQ ID NO 3
<211> LENGTH: 26
<212> TYPE: DNA
<213> ORGANISM: Artificial Sequence
<220> FEATURE:
<223> OTHER INFORMATION: Primer
```

```
<400> SEQUENCE: 3
ccccacaaac cccattacta aaccca                                          26
```